(12) United States Patent
Sugiyama

(10) Patent No.: US 11,447,740 B2
(45) Date of Patent: Sep. 20, 2022

(54) LACTIC ACID BACTERIUM AND USE THEREOF

(71) Applicant: Sone Farm Co., Ltd., Tokyo (JP)

(72) Inventor: Masanori Sugiyama, Hiroshima (JP)

(73) Assignee: SONE FARM CO., LTD., Tokyo (JP)

( * ) Notice: Subject to any disclaimer, the term of this patent is extended or adjusted under 35 U.S.C. 154(b) by 233 days.

(21) Appl. No.: 16/317,397

(22) PCT Filed: May 28, 2018

(86) PCT No.: PCT/JP2018/020333
§ 371 (c)(1),
(2) Date: Jan. 11, 2019

(87) PCT Pub. No.: WO2018/225556
PCT Pub. Date: Dec. 13, 2018

(65) Prior Publication Data
US 2019/0390289 A1 Dec. 26, 2019

(30) Foreign Application Priority Data
Jun. 9, 2017 (JP) .............................. JP2017-114171

(51) Int. Cl.
| | | |
|---|---|---|
| *C12N 1/20* | (2006.01) | |
| *A23K 10/18* | (2016.01) | |
| *A23L 19/00* | (2016.01) | |
| *A23L 33/135* | (2016.01) | |
| *A61P 39/00* | (2006.01) | |
| *A61K 8/99* | (2017.01) | |
| *A61K 35/747* | (2015.01) | |
| *A61Q 19/00* | (2006.01) | |
| *C12P 19/04* | (2006.01) | |
| *C12R 1/225* | (2006.01) | |

(52) U.S. Cl.
CPC .............. *C12N 1/205* (2021.05); *A23K 10/18* (2016.05); *A23L 19/09* (2016.08); *A23L 33/135* (2016.08); *A61K 8/99* (2013.01); *A61K 35/747* (2013.01); *A61P 39/00* (2018.01); *A61Q 19/00* (2013.01); *C12N 1/20* (2013.01); *C12P 19/04* (2013.01); *A23V 2002/00* (2013.01); *A23Y 2220/63* (2013.01); *C12R 2001/225* (2021.05)

(58) Field of Classification Search
CPC ................................. C12R 1/225; A23K 10/18
See application file for complete search history.

(56) References Cited

U.S. PATENT DOCUMENTS

| | | | |
|---|---|---|---|
| 8,557,561 | B2 | 10/2013 | Chambaud et al. |
| 9,161,957 | B2 | 10/2015 | Smith et al. |
| 10,059,919 | B2 | 8/2018 | Hornbaek et al. |
| 10,251,407 | B2 | 4/2019 | Budelli et al. |
| 2011/0150838 | A1 | 6/2011 | Chang et al. |
| 2011/0150852 | A1 | 6/2011 | Chambaud et al. |
| 2014/0050702 | A1 | 2/2014 | Smith et al. |
| 2014/0377238 | A1 | 12/2014 | Budelli et al. |
| 2015/0064152 | A1 | 3/2015 | Hornbaek et al. |

FOREIGN PATENT DOCUMENTS

| | | |
|---|---|---|
| EP | 2271744 A2 | 1/2011 |
| EP | 2338977 A1 | 6/2011 |
| EP | 2734049 A2 | 5/2014 |
| EP | 2836588 A1 | 2/2015 |
| EP | 2879686 A1 | 6/2015 |
| JP | 2006298779 A | 11/2006 |
| JP | 2010252641 A | 11/2010 |
| JP | 2011517570 A | 6/2011 |
| JP | 2011142907 A | 7/2011 |
| JP | 2014516589 A | 7/2014 |
| JP | 2015519042 A | 7/2015 |
| JP | 2015525780 A | 9/2015 |
| JP | 2016037451 A | 3/2016 |
| KR | 20130092182 A | 8/2013 |
| WO | 2009130423 A2 | 10/2009 |
| WO | 2009131208 A1 | 10/2009 |
| WO | 2011076007 A1 | 6/2011 |
| WO | 2012133827 A1 | 10/2012 |
| WO | 2012136830 A1 | 10/2012 |
| WO | 2012177556 A2 | 12/2012 |
| WO | 2014022279 A1 | 2/2014 |

OTHER PUBLICATIONS

Benyacoub J. et al. Immune modulation property of Lactobacillus paracasei NCC2461 (ST11) strain and impact on skin defences. (2013). 5(2), 129-136 (Year: 2013).*
BLAST—NCBI website sequence alignment results. PDF copy provided (Year: 2021).*
Chen YP, Hsu CA, Hung WT, Chen MJ. Effects of Lactobacillus paracasei 01 fermented milk beverage on protection of intestinal epithelial cell in vitro. J Sci Food Agric. Apr. 2016;96(6):2154-60 (Year: 2016).*
FDA_Cosmetic (Website. PDF copy provided. Accessed Jan. 13, 2021) (Year: 2021).*
Living Nature (Website, archive from Oct. 2014 retrieved on Jan. 13, 2021. https://www.livingnature.com/pages/healthy-skin-is-beautiful-skin. Copy provided.) (Year: 2014).*
Wang (GenBank Accession #CP007122.1). (Year: 2014).*
Wang et al., "Effects of Lactobacillus plantarum MA2 isolated from Tibet kefir on lipid metabolism and intestinal microflora of rats fed on high-cholesterol diet" Appl Microbiol Biotechnol, 84:341-347 (2009).

(Continued)

*Primary Examiner* — Vera Afremova
(74) *Attorney, Agent, or Firm* — Venable LLP; Henry J. Daley

(57) ABSTRACT

A new lactic acid bacterium of the present invention produces, as an exopolysaccharide, a neutral polysaccharide having a structure in which N-acetylglucosamines are linked with each other via α-1,6 bond, is obtained from a fig, has a hyaluronidase inhibitory, an anti-alcoholic damage activity effect, and the like, and is therefore useful in a food and drink, a medicine, a feed, a cosmetic and the like exerting an antiallergy effect, an anti-alcoholic damage effect, and the like.

9 Claims, 10 Drawing Sheets

Specification includes a Sequence Listing.

(56) References Cited

OTHER PUBLICATIONS

Nguyen et al., "Characterization of Lactobacillus plantarum PH04, a potential probiotic bacterium with cholesterol-lowering effects" International Journal of Food Microbiology 113:358-361 (2007).

Zhao et al., "The Obesity and Fatty Liver are Reduced by Plant-Derived Pediococcus pentosaceus LP28 in High Fat Diet-Induced Obese Mice"(PLoS ONE 7(2):1-8 (2012).

Ichikawa et al., "Orally Administered Lactobacillis paracasei KW3110 Induces in Vivo IL-12 Production" Biosci. Biotechnol. Biochem., 73(7):1561-1565 (2009).

Náacher-Vázquez et al., "Dextrans produced by lactic acid bacteria exhibit antiviral andimmunomodulatory activity against salmonid viruses" Carbohydrate Polymers 124:292-301 (2015).

Nagaoka et al., "Anti-ulcer Effects of Lactic Acid Bacteria and Their Cell Wall Polysaccharides" Biol. Pharm. Bull 17 (8):1012-1017 (1994).

Balzaretti et al., "A Novel Rhamnose-Rich Heteroexopolysaccharide Isolated from Lactobacillus paracasei DG Activates THP-1 Human Monocytic Cells" 83(3):1-15, Applied and Environmental Microbiology (2017).

Kang et al., "Exopolysaccharide-Overproducing Lactobacillus paracasei KB28 Induces Cytokines in Mouse Peritoneal Macrophages via Modulation of NF-?B and MAPKs"J. Microbiol. Biotechnol. 21(11):1174-1178 (2011).

Robijn et al., "Structural studies of the exopolysaccharide produced by Lactobacillus paracasei 34-1" Carbohydrate Research (285): I29-139 (1996).

Database DDBJ/EMBL/GenBank [online], Accession No. CP007122.1, <<https://www.ncbi.nlm.nih.gov/nuccore/CP007122.1?from=1960345&to=1961923&report=gbw> ithparts&strand=2>, Oct. 1, 2014 uploaded [retrieved on Jul. 20, 2018], Wang, S., et al., Definition: Lactobacillus paracasei N1115, complete genome [Definition] [Features][Origin] sections.

Panthavee et al., "Characterization of Exopolysaccharides Produced by Thermophilic Lactic Acid Bacteria Isolated from Tropical Fruits of Thailand" Biol. Pharm Bull 40:621-629 (2017).

International Search Report issued in corresponding PCT/JP2018/020333, dated Aug. 14, 2018 (with English translation).

Noda, M. et al., "A novel structure of exopolysaccharide produced by a plant-derived lactic acid bacterium Lactobacillus paracasei IJH-SONE68" J. Biochem, 164(2):87-92, p. 87 (abstract), p. 88 (FIG.1), p. 89(FIG. 2), p. 90 (table 3) (2018).

Noda et al., "Exopolysaccharide Produced by Lactobacillus paracasei IJH-SONE68 Prevents and improves the Picryl Chloride-Induced Contact Dermatitis", Molecules Online, vol. 24, No. 16, 2970, Aug. 16, 2019, pp. 1-14; XP055618376.

* cited by examiner

FIG.1
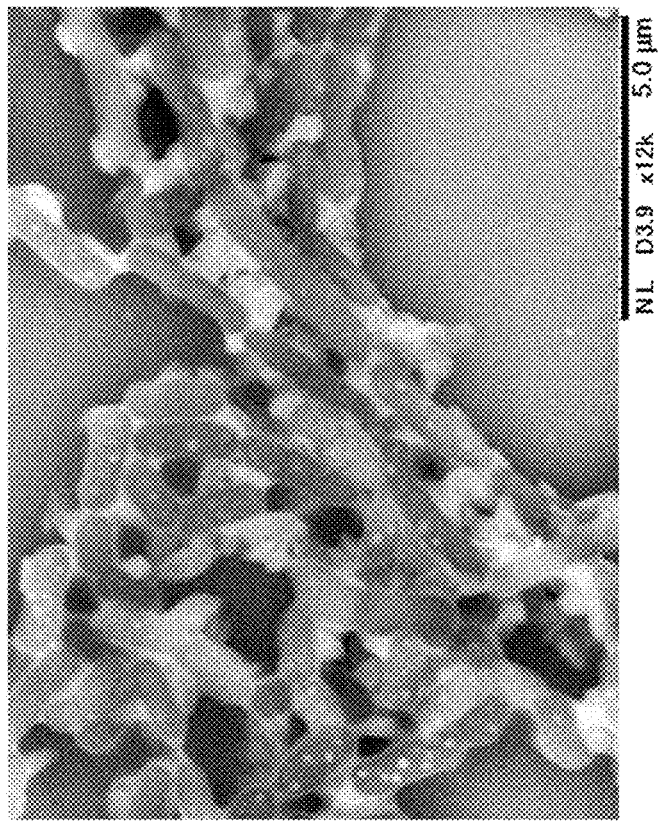
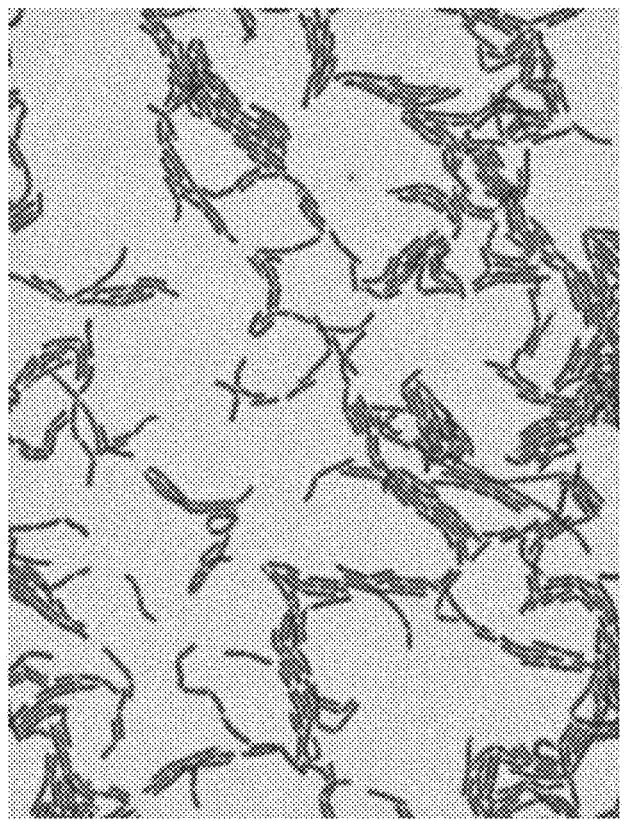

FIG.4 Structural analysis of neutral exopolysaccharide

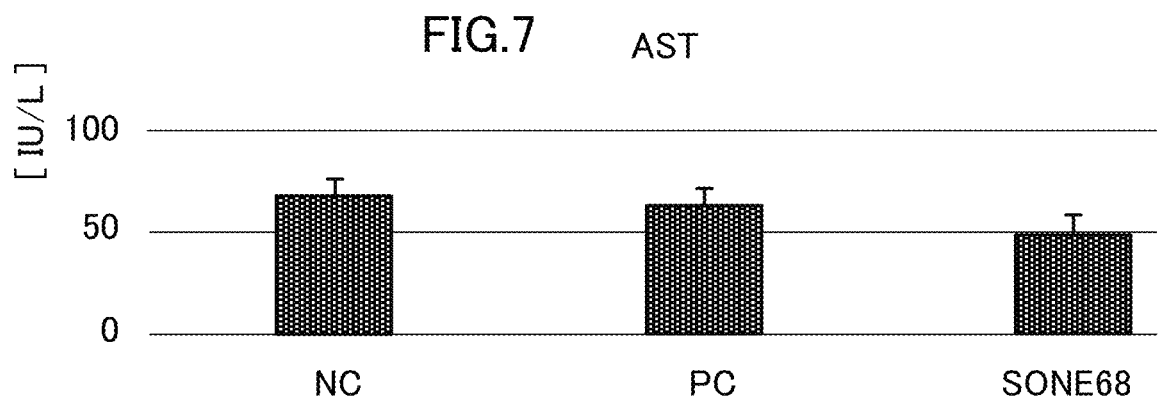
FIG.7 AST
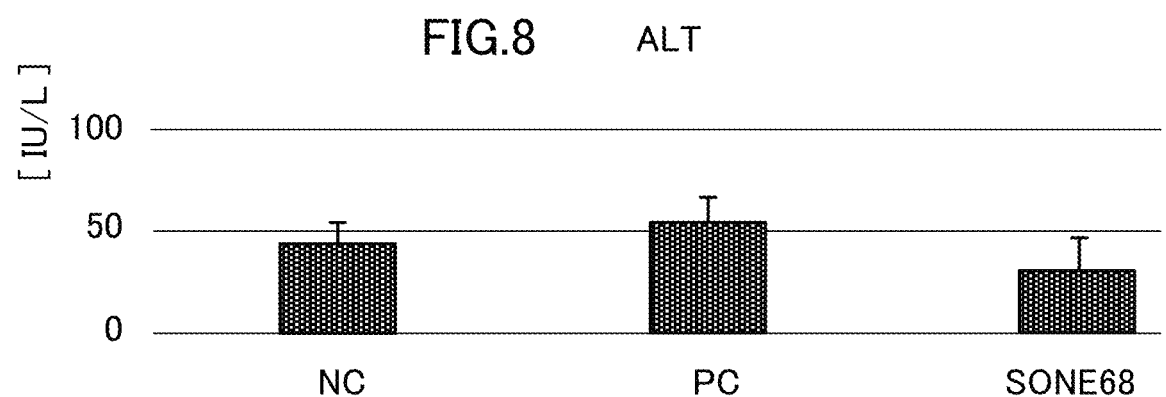
FIG.8 ALT
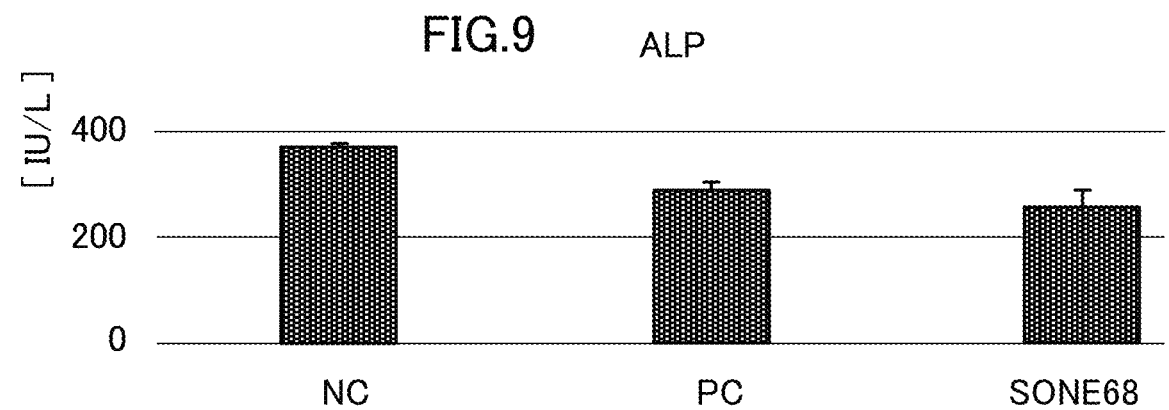
FIG.9 ALP

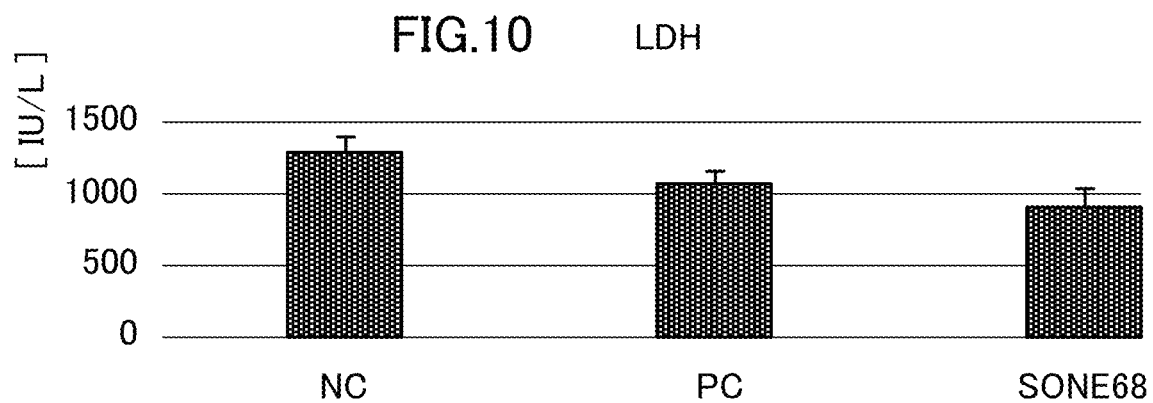
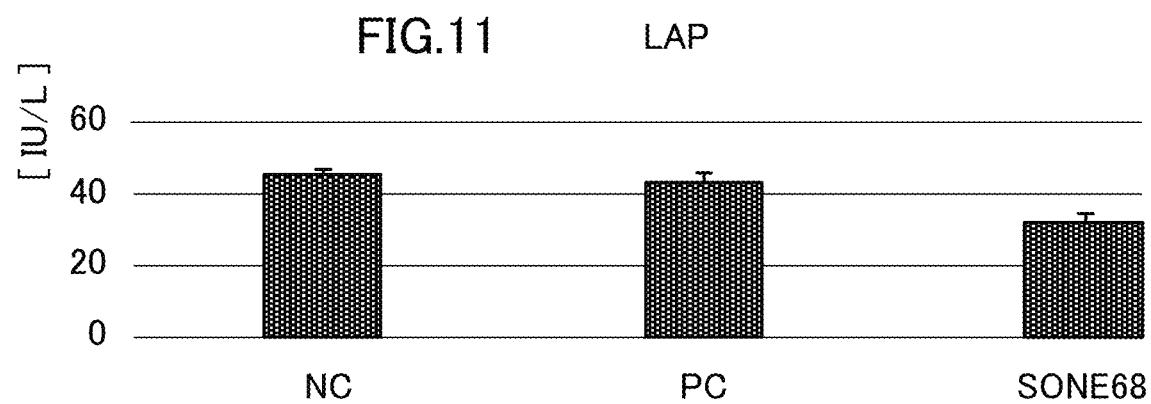
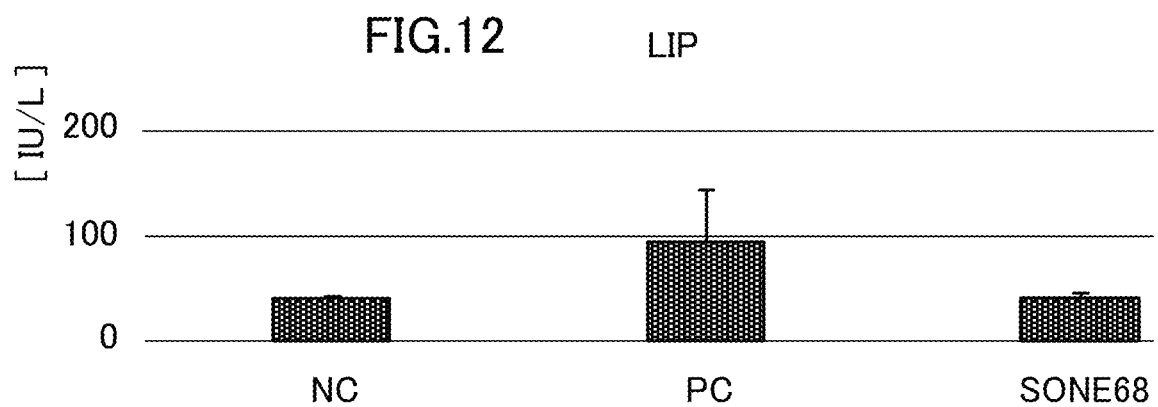

After cultivation, turbidity was observed only on SONE68 strain.

Remarkable proliferation was observed only on SONE68 strain.

LACTIC ACID BACTERIUM AND USE THEREOF

This application is a National Stage Application under 35 U.S.C. § 371 PCT/JP2018/020333, filed May 28, 2018, which claims priority benefit from Japanese Patent Application No. 2017-114171, filed on Jun. 9, 2017, the entire content of which is incorporated herein by reference. All references cited anywhere in this specification, including the Background and Detailed Description sections, are incorporated by reference as if each had been individually incorporated.

SEQUENCE LISTING

The instant application contains a Sequence Listing which has been filed electronically in ASCII format and is hereby incorporated by reference in its entirety. Said ASCII copy, created on Aug. 22, 2019, is named 36595_496064_SL.txt and is 2,876 bytes in size.

TECHNICAL FIELD

The present invention relates to a new lactic acid bacterium and the use thereof. More specifically, the present invention relates to a new lactic acid bacterium that produces, as an exopolysaccharide, a neutral polysaccharide having a structure wherein N-acetylglucosamines are linked with each other via $\alpha$-1,6-bond, and a composition, such as a food and drink composition and a pharmaceutical composition, comprising the new lactic acid bacterium and exerting an antiallergy effect and the like.

BACKGROUND ART

Lactic acid bacteria are a group of bacteria that ferment carbohydrates such as glucose to acquire energy, produce a large amount of lactic acid and are nonpathogenic and non-spore-forming gram-positive bacteria. Lactic acid bacteria have been used for the preparation of fermented foods such as yogurt and cheese for a long time and are widely used as probiotics because they exert a beneficial effect for the health care of hosts when administered at an appropriate dose.

For example, *Lactobacillus plantarum* strain MA2 (Non-Patent Document 1) having an effect on serum lipid, *Lactobacillus plantarum* strain PH04 having an action of reducing cholesterol (Non-Patent Document 2), and the like are known as lactic acid bacteria effective as probiotics. In addition, *Pediococcus pentosaceus* strain LP28 (Non-Patent Document 3) having an effect of improving fatty liver and suppressing accumulation of fat in vivo, and the like are known as plant-derived lactic acid bacteria.

*Lactobacillus paracasei* strain K71 having an antiallergy action (Patent Document 1), *Lactobacillus paracasei* strain MCC1375 having an anti-influenza virus activity (Patent Document 2), *Lactobacillus paracasei* strain KW3110 which activates interleukin-12 production (Non-Patent Document 4), and the like are also known as lactic acid bacteria strains belonging to *Lactobacillus paracasei*.

Some lactic acid bacterial strains are known to produce exopolysaccharides as physiologically active substances that contribute to the maintenance and improvement of human health. It has been shown that exopolysaccharides produced by lactic acid bacteria exert an immunomodulatory function and an anti-gastritis effect (Non-Patent Documents 5 and 6). In addition, exopolysaccharides produced by lactic acid bacteria belonging to *Lactobacillus paracasei* are also known, and it has been reported that *Lactobacillus paracasei* strain DG produces rhamnose-rich exopolysaccharides (Non-Patent Document 7), and that *Lactobacillus paracasei* strain KB28 produces glucose-rich exopolysaccharides (Non-Patent Document 8). It has also been reported that *Lactobacillus paracasei* strain 34-1 produces an exopolysaccharide composed of D-galactose, 2-acetamido-2-deoxy-D-galactose and sn-glycerol 3-phosphate (Non-Patent Document 9).

PRIOR ART DOCUMENTS

Patent Documents

Patent Document 1: WO2009/131208
Patent Document 2: WO2012/133827

Non-Patent Documents

Non-Patent Document 1: Appl. Microbiol. Biotechnol., 84, 341-347 (2009)
Non-Patent Document 2: Int. J. Food Microbiol., 113, 358-361 (2007)
Non-Patent Document 3: PLoS One e30696 (2012)
Non-Patent Document 4: Biosci. Biotechnol. Biochem., 73, 1561-1565
Non-Patent Document 5: Carbohydr. Polym., 124, 292-301 (2015)
Non-Patent Document 6: Biol. Pharm. Bull., 17, 1012-1017 (1994)
Non-Patent Document 7: Appl. Environ. Microbiol., 83, e02702-16 (2017)
Non-Patent Document 8: J. Microbiol. Biotechnol., 21, 1174-1178 (2011)
Non-Patent Document 9: Carbohdr. Res., 285, 129-139 (1996)

SUMMARY OF INVENTION

Problem to be Solved by Invention

In light of the background art, the further development of novel lactic acid bacteria that are useful as new probiotics has been desired. Therefore, the problem to be solved by the present invention is to provide a novel lactic acid bacterium that is expected as a new probiotic and is effective as an active ingredient of a composition such as a food and drink composition or a pharmaceutical composition, and the use thereof.

Means for Solving the Problem

The inventors of the present invention, as a result of intensive studies for the purpose of developing a novel lactic acid bacterium useful as a new probiotic, found that a lactic acid bacterium producing a novel neutral polysaccharide having a structure which has not at all been observed in conventional lactic acid bacteria and in which N-acetylglucosamines are linked with each other via $\alpha$-1,6 bond can be obtained from a fig, and further continued studies on the basis of such findings, then completed the present invention.

In one aspect of the present invention, the present invention relates to a lactic acid bacterium that produces, as an exopolysaccharide, a neutral polysaccharide having a structure in which N-acetylglucosamines are linked with each other via $\alpha$-1,6 bond.

The lactic acid bacterium is preferably a lactic acid bacterium belonging to *Lactobacillus*, and particularly preferably a lactic acid bacterium belonging to *Lactobacillus paracasei*. In addition, the lactic acid bacterium of the present invention is preferably a lactic acid bacterium derived from a FIG. In particular, *Lactobacillus paracasei* strain IJH-SONE68 (Accession No. NITE BP-02242) or a lactic acid bacterium equivalent thereto is preferable.

In addition, the neutral polysaccharide produced by the lactic acid bacterium particularly has a hyaluronidase inhibitory activity.

In other aspect of the present invention, the present invention relates to a composition comprising the lactic acid bacterium as described above.

The composition is preferably a food and drink composition, and the food and drink preferably include a beverage, a functional food, a fermented food and a supplement. In addition, the composition is preferably a pharmaceutical composition, a feed composition and a cosmetic composition.

These compositions are preferably used for a hyaluronidase inhibition, an antiallergy, an anti-alcoholic damage, and the like.

Effect of Invention

A polysaccharide such as a neutral polysaccharide, which is produced by the lactic acid bacterium of the present invention as an exopolysaccharide, exhibits an activity of inhibiting hyaluronidase that is an enzyme hydrolyzing hyaluronic acid, so that the lactic acid bacterium of the present invention is effective as a food and drink, a supplement, a medicine and a feed which each exert an antiallergy effect and the like. In addition, the lactic acid bacterium of the present invention has an effect of reducing AST (aspartate aminotransferase), ALT (alanine aminotransferase), ALP (alkaline phosphatase) and the like, which are indications for investigating alcoholic damage, in serum of an alcoholic hepatitis-induced mouse model, and is therefore effective as a food and drink or a medicine for anti-alcoholic damage.

Furthermore, the lactic acid bacterium of the present invention has a high resistance against gastric acid and bile acid and is therefore particularly effective as a food and drink, a supplement and a medicine which each exert their efficacy in the gastrointestinal tract of humans, and a feed of mammals, livestock, pet animals and the like.

In addition, since the lactic acid bacterium of the present invention exerts a strong proliferation ability even in a medium using egg white, it has a strong defense mechanism against lysozyme degrading bacterial cell wall and transferrin interfering the iron utilization of bacteria by their chelating action, which are enzymes present in egg white. From this aspect too, the lactic acid bacterium of the present invention can be effectively used as a food and drink and a medicine.

In addition, the lactic acid bacterium of the present invention has an assimilation ability characterized in that it cannot assimilate amygdalin that may generate hydrocyanic acid when decomposed, or arbutin that is reported to inhibit melanin production thereby to exert whitening effect. Furthermore, as described above, the lactic acid bacterium of the present invention exhibits a strong proliferation ability even in a medium using egg white, and it can be therefore effectively used as a cosmetic product together with, for example, egg white.

BRIEF DESCRIPTION OF DRAWINGS

FIG. 1 is microscope photographs of *Lactobacillus paracasei* strain IJH-SONE 68 isolated and identified according to the present invention. (A) in FIG. 1 is a gram-stained microscope photograph, and (B) in FIG. 1 is a scanning electron microscope (SEM) photograph.

FIG. 6 illustrates at (B) the correspondences between pce1 gene cluster of *Lactobacillus paracasei* strain IJH-SONE68 and a gene cluster of strain JCM8130T.

FIG. 7 is a graph illustrating the influence of *Lactobacillus paracasei* strain JH-SONE68 on AST (alanine aminotransferase) in serum of an alcoholic hepatitis-induced mouse model.

FIG. 8 is a graph illustrating the influence of *Lactobacillus paracasei* strain JH-SONE68 on ALT (aspartate aminotransferase) in serum of an alcoholic hepatitis-induced mouse model.

FIG. 9 is a graph illustrating the influence of *Lactobacillus paracasei* strain IJH-SONE68 on ALP (alkaline phosphatase) in serum of an alcoholic hepatitis-induced mouse model.

FIG. 10 is a graph illustrating the influence of *Lactobacillus paracasei* strain IJH-SONE68 on LDH (lactate dehydrogenase) in serum of an alcoholic hepatitis-induced mouse model.

FIG. 11 is a graph illustrating the influence of *Lactobacillus paracasei* strain IJH-SONE68 on LAP (leucine aminopeptidase) in serum of an alcoholic hepatitis-induced mouse model.

FIG. 12 is a graph illustrating the influence of *Lactobacillus paracasei* strain IJH-SONE68 on LIP (lipase) in serum of an alcoholic hepatitis-induced mouse model.

EMBODIMENTS FOR CARRYING OUT INVENTION

Figure 2:
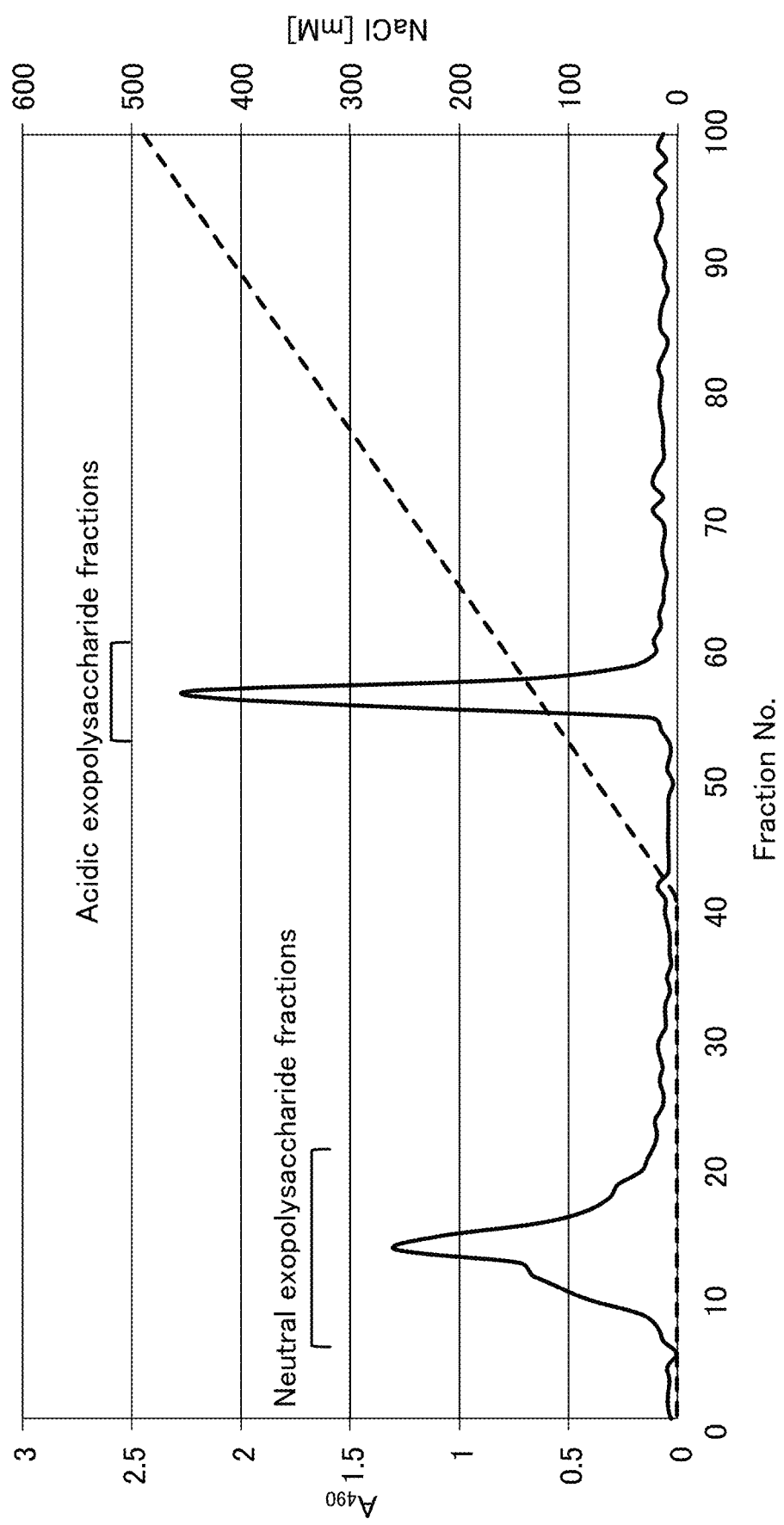
FIG. 2 illustrates an isolation profile of anion exchange chromatography (TOYOPEARL DEAE-650M resin (Tosoh Corporation)) of exopolysaccharides from *Lactobacillus paracasei* strain IJH-SONE68. The exopolysaccharides were eluted with NaCl having a gradient concentration of 0 mM to 500 mM (broken line), and the exopolysaccharide in each fraction was monitored at 490 nm by a phenol sulfuric acid method (straight line).

The lactic acid bacterium of the present invention and use thereof are described below in detail.

1. The Lactic Acid Bacterium of the Present Invention

The lactic acid bacterium of the present invention is a lactic acid bacterium that produces, as an exopolysaccharide, a neutral polysaccharide having a structure in which N-acetylglucosamines are linked with each other via α-1,6 bond. A lactic acid bacterium that produces, as an exopolysaccharide, a neutral polysaccharide having a structure in which N-acetylglucosamines are linked with each other via α-1,6 bond has not been known in the past, and have for the first time been found by the present invention. The lactic acid bacterium of the present invention may be any lactic acid bacterium as long as it is a lactic acid bacterium that produces a neutral polysaccharide having such a specific structure, and is not limited to a specific lactic acid bacterium.

The lactic acid bacterium of the present invention includes lactic acid bacteria belonging to genus *Lactobacillus*, genus *Leuconostoc*, genus *Streptococcus*, genus *Pediococcus*, genus *Melissococcus*, genus *Enterococcus*, genus *Trichococcus*, genus *Lactococcus*, genus *Carnobacterium*, genus *Vagococcus*, genus *Tetragenococcus*, *Atopobium*, genus *Weissella*, genus *Oenococcus*, genus *Abiotrophia*, genus *Desemzia*, genus *Paralactobacillus*, genus *Granulicatella*, genus *Alkalibacterium*, genus *Olsenella*, genus *Isobaculum*, genus *Marinilactibacillus*, genus *Atopostipes*, genus *Lactovum*, genus *Pilibacter*, genus *Fructobacillus*, genus *Lacticigemium*, genus *Bavariicoccus*, genus *Bifidobacterium*, and the like. In particular, lactic acid bacteria belonging to genus *Lactobacillus* are preferred.

Lactic acid bacteria belonging to genus *Lactobacillus* include *Lactobacillus paracasei*, *Lactobacillus acetotolerans*, *Lactobacillus acidifarinae*, *Lactobacillus acidipiscis*, *Lactobacillus acidophilus*, *Lactobacillus agilis*, *Lactobacillus algidus*, *Lactobacillus Alimentarius*, *Lactobacillus amylolyticus*, *Lactobacillus amylophilus*, *Lactobacillus amylotrophicus*, *Lactobacillus amylovorus*, *Lactobacillus animalis*, *Lactobacillus antri*, *Lactobacillus apodeme*, *Lactobacillus aquaticus*, *Lactobacillus aviaries*, *Lactobacillus bifermentans*, *Lactobacillus bobalius*, *Lactobacillus brevis*, *Lactobacillus buchneri*, *Lactobacillus cacaonum*, *Lactobacillus camelliae*, *Lactobacillus capilatus*, *Lactobacillus casei*, *Lactobacillus catenaformis*, *Lactobacillus ceti*, *Lactobacillus coleohominis*, *Lactobacillus collinoides*, *Lactobacillus composti*, *Lactobacillus concavus*, *Lactobacillus coryniformis*, *Lactobacillus crispatus*, *Lactobacillus crustorum*, *Lactobacillus curvatus*, *Lactobacillus delbrueckii* subsp. *Bulgaricus*, *Lactobacillus delbrueckii* subsp. *Delbrueckii*, *Lactobacillus delbrueckii* subsp. *Indicus*, *Lactobacillus delbrueckii* subsp. *Lactis*, *Lactobacillus dextrinicus*, *Lactobacillus diolivorans*, *Lactobacillus equi*, *Lactobacillus equigenerosi*, *Lactobacillus fabifermentans*, *Lactobacillus farciminis*, *Lactobacillus farraginis*, *Lactobacillus fermentum*, *Lactobacillus fornicalis*, *Lactobacillus fructivorans*, *Lactobacillus frumenti*, *Lactobacillus fuchuensis*, *Lactobacillus gallinarum*, *Lactobacillus gasseri*, *Lactobacillus gastricus*, *Lactobacillus ghanensis*, *Lactobacillus graminis*, *Lactobacillus hammesii*, *Lactobacillus hamster*, *Lactobacillus harbinensis*, *Lactobacillus hayakitensis*, *Lactobacillus helveticus*, *Lactobacillus hilgardii*, *Lactobacillus homohiochii*, *Lactobacillus hordei*, *Lactobacillus iners*, *Lactobacillus ingluviei*, *Lactobacillus intestinalis*, *Lactobacillus jensenii*, *Lactobacillus johnsonii*, *Lactobacillus kalixensis*, *Lactobacillus kefiranofaciens*, *Lactobacillus kefiri*, *Lactobacillus kimchi*, *Lactobacillus kisonensis*, *Lactobacillus kitasatonis*, *Lactobacillus kunkeei*, *Lactobacillus leichmannii*, *Lactobacillus lindneri*, *Lactobacillus malefermentans*, *Lactobacillus mali*, *Lactobacillus manihotivorans*, *Lactobacillus mindensis*, *Lactobacillus mucosae*, *Lactobacillus murinus*, *Lactobacillus nagelii*, *Lactobacillus namurensis*, *Lactobacillus nantensis*, *Lactobacillus nodensis*, *Lactobacillus oligofermentans*, *Lactobacillus oris*, *Lactobacillus otakiensis*, *Lactobacillus panis*, *Lactobacillus pantheris*, *Lactobacillus parabrevis*, *Lactobacillus parabuchneri*, *Lactobacillus paracollinoides*, *Lactobacillus parafarraginis*, *Lactobacillus parakefiri*, *Lactobacillus paralimentarius*, *Lactobacillus paraplantarum*, *Lactobacillus pentosus*, *Lactobacillus perolens*, *Lactobacillus plantarum*, *Lactobacillus pontis*, *Lactobacillus psittaci*, *Lactobacillus rapi*, *Lactobacillus rennini*, *Lactobacillus reuteri*, *Lactobacillus rhamnosus*, *Lactobacillus rimae*, *Lactobacillus rossiae*, *Lactobacillus ruminis*, *Lactobacillus saerimneri*, *Lactobacillus sakei*, *Lactobacillus salivarius*, *Lactobacillus sanfranciscensis*, *Lactobacillus satsumensis*, *Lactobacillus secaliphilus*, *Lactobacillus senmaizukei*, *Lactobacillus sharpeae*, *Lactobacillus siliginis*, *Lactobacillus spicheri*, *Lactobacillus suebicus*, *Lactobacillus sunkii*, *Lactobacillus susicola*, *Lactobacillus taiwanensis*, *Lactobacillus thailandensis*, *Lactobacillus tucceti*, *Lactobacillus ultunensis*, *Lactobacillus uvarum*, *Lactobacillus vaccinostercus*, *Lactobacillus vaginalis*, *Lactobacillus versmoldensis*, *Lactobacillus vini*, *Lactobacillus vitulinus*, *Lactobacillus zeae* and *Lactobacillus zymae*. In particular, *Lactobacillus paracasei* is preferred.

Among these lactic acid bacteria, the lactic acid bacterium of the present invention is preferably a lactic acid bacterium derived from a fig. Specifically, according to the present invention, *Lactobacillus paracasei* strain IJH-SONE68 was isolated and identified from leaves of a fig, as a lactic acid bacterium that produces, as an exopolysaccharide, a neutral polysaccharide having a structure in which N-acetylglucosamines are linked with each other via α-1,6 bond. This strain was nationally deposited under the accession number of NITE P-02242 at Patent Microorganisms Depositary, National Institute of Technology and Evaluation (#122, 2-5-8 Kazusakamatari, Kisarazu-shi, Chiba 292-0818, Japan) on Apr. 19, 2016. The deposition was then transferred to an international deposit under the Budapest Treaty and given the international deposit accession number of NITE BP-02242 on May 26, 2017.

As illustrated in the photograph of FIG. 1, *Lactobacillus paracasei* strain IJH-SONE68 isolated and identified from leaves of a fig is a catalase-negative, gram-positive *bacillus*, and has mycological properties of forming a white colony and the characteristic of conditional heterolactic fermentation. Furthermore, the strain has an ability to produce a polysaccharide, in particular, a neutral polysaccharide having a structure in which N-acetylglucosamines are linked with each other via α-1,6 bond.

Figure 3:
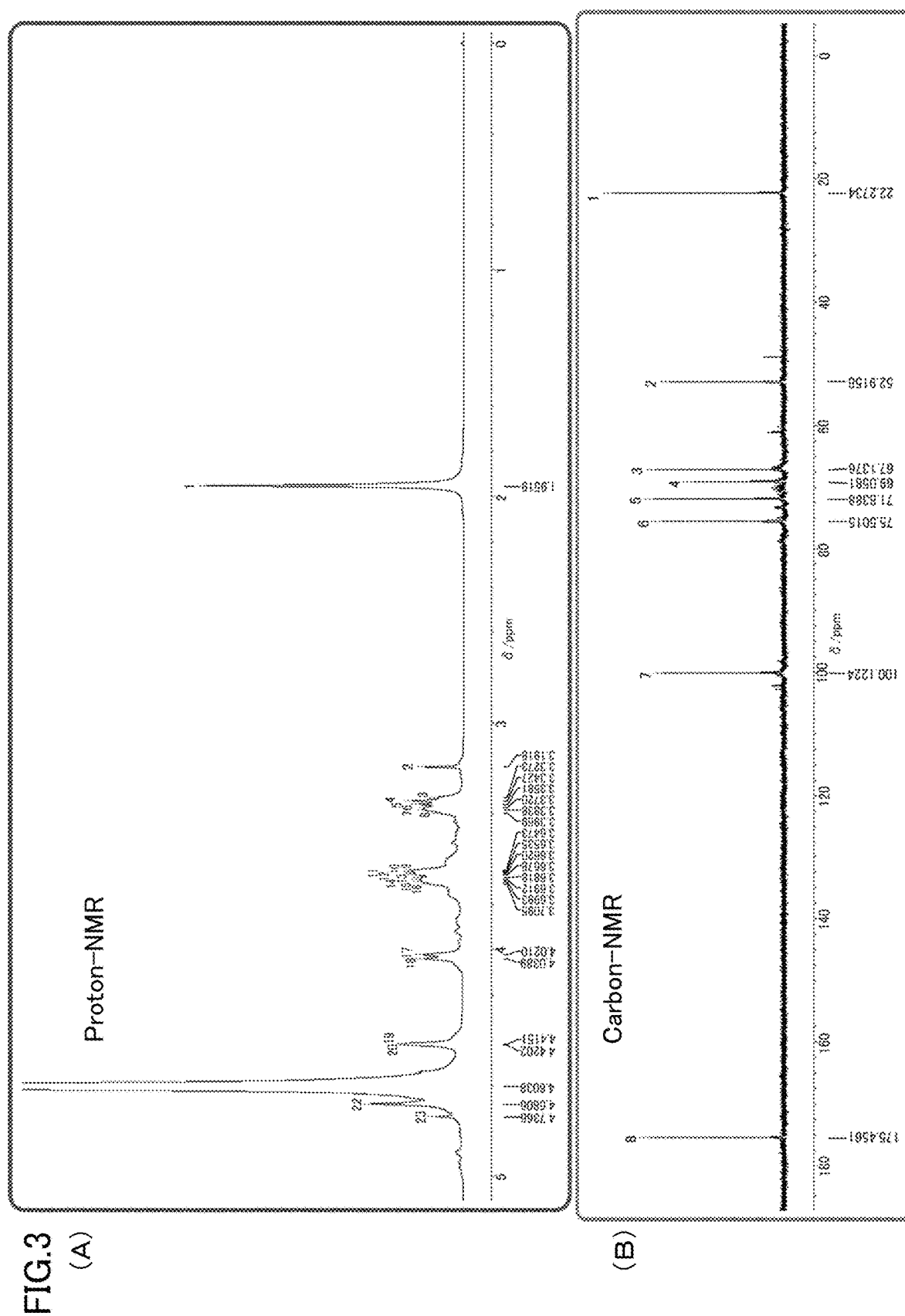
FIG. 3 illustrates each NMR profile obtained by subjecting a neutral exopolysaccharide, which was obtained by purifying exopolysaccharides from *Lactobacillus paracasei* strain IJH-SONE68 with anion exchange column chromatography, to proton-NMR and carbon-NMR. (A) in FIG. 3 is the NMR profile of proton-NMR, and (B) in FIG. 3 is the NMR profile of carbon-NMR.

This neutral polysaccharide is obtained by separating and purifying polysaccharides obtained from the culture of *Lactobacillus paracasei* strain IJH-SONE68, according to an anion exchange chromatography, as described in Example 4 provided hereinbelow. The NMR profiles of proton-NMR and carbon-NMR as illustrated in FIG. 3 have revealed that this neutral polysaccharide has a structure in which N-acetylglucosamines are linked with each other via α-1,6 bond.

In addition, *Lactobacillus paracasei* strain IJH-SONE68 has an ability of assimilating sugars, as shown in Table 1 of Example 3 provided hereinafter. In particular, as compared with other *Lactobacillus paracasei*, *Lactobacillus paracasei* strain IJH-SONE68 has a sugar-assimilating ability characterized in that it cannot assimilate amygdalin that may generate hydrocyanic acid when decomposed, or arbutin that is reported to inhibit melanin production thereby to exert a whitening effect.

From analysis of the whole genome sequence of *Lactobacillus paracasei* strain IJH-SONE68, it has been predicted that the genomic DNA of *Lactobacillus paracasei* strain IJH-SONE68 consists of 3,084,917 bp with a GC content of 46.37%, and has 2,963 structural genes. Furthermore, it has been shown that *Lactobacillus paracasei* strain IJH-SONE68 has two plasmids, one of which has a size of at least 51 kb, and the other has a size of 45,267 bp. As compared with other lactic acid bacteria, *Lactobacillus paracasei* strain IJH-SONE68 has a larger genome size and the larger number of structural genes.

In addition, two exopolysaccharide biosynthesis gene clusters have been found in the genomic DNA sequence of *Lactobacillus paracasei* strain IJH-SONE68, one of the two clusters is 23 kb cluster which has been named pce1 cluster, and other cluster is 28 kb cluster which has been named pce2 cluster. It has been then found that a protein deduced from a gene, which is one of glycosyltransferase genes in the pce2 cluster and which has been named pce2J, has a motif or domain similar to pfam02485 motif or domain observed in β-1,6-N-acetylglucosaminyltransferase that has already been known (Genes Dev., 1993 March; 7(3): 468-478, and J. Biol. Chem., 1999 Jan. 29; 274(5): 3215-3221). Hence, it has been suggested that this structural gene in pce2 cluster is involved in a biosynthesis of the neutral polysaccharide.

In the present invention, the lactic acid bacterium of the present invention also includes a lactic acid bacteria equivalent to *Lactobacillus paracasei* strain IJH-SONE68. Here, the equivalent lactic acid bacterium indicates a lactic acid bacterium that belongs to *Lactobacillus paracasei* and has an ability of producing a neutral polysaccharide having a structure in which N-acetylglucosamines are linked with each other via α-1,6 bond. In addition, the equivalent lactic acid bacterium indicates a bacterial strain which belongs to *Lactobacillus paracasei*, 16S rDNA gene of which has a base sequence having 98% or more, preferably 99% or more, more preferably 100% identity with the base sequence of SEQ ID NO: 3 of 16S rDNA gene of *Lactobacillus paracasei* strain IJH-SONE68, and which preferably has the same microbial properties and/or the same sugar-assimilating ability as those of *Lactobacillus paracasei* strain IJH-SONE68. In addition, the equivalent lactic acid bacterium indicates a bacterial strain which belongs to *Lactobacillus paracasei* and have the same biological activities as those of *Lactobacillus paracasei* strain IJH-SONE68, such as an antiallergy action, an anti-alcoholic damage action, and an acid resistance.

These equivalent lactic acid bacteria are obtained, for example, by performing usual mutation treatment technique, such as mutation and genetic recombination, on *Lactobacillus paracasei* strain IJH-SONE68 and, in addition, may be bacterial strains that has been bred by selecting natural mutation strains of *Lactobacillus paracasei* strain IJH-SONE68, and the like.

2. Obtainment and Proliferation of the Lactic Acid Bacterium of the Present Invention The lactic acid bacterium of the present invention is obtained by isolating exopolysaccharides produced by a lactic acid bacterium in the same manner as the separation and purification of polysaccharides produced by *Lactobacillus paracasei* strain IJH-SONE68 as described in Example 4 provided hereinafter, and investigating whether the separated and purified polysaccharide is a neutral polysaccharide having a structure in which N-acetylglucosamines are linked with each other via α-1,6 bond.

The lactic acid bacterium of the present invention can be easily proliferated by culturing those obtained bacteria. The culture method is not limited to a specific one as long as it is capable of proliferating a lactic acid bacterium, and a method commonly used for culturing a lactic acid bacterium may be used as it is, or a method that is appropriately modified if necessary may be used. For example, the culture temperature may be usually 25 to 50° C., preferably 35 to 42° C. The cultivation may be performed under either aerobic or anaerobic condition, particularly preferably under anaerobic condition. For example, the cultivation may be performed while ventilating anaerobic gas such as carbon dioxide gas or nitrogen gas at an appropriate concentration. In addition, the cultivation may be also performed under microaerobic condition such as liquid static culture.

The medium for culturing a lactic acid bacterium is not particularly limited, but a medium usually used for culturing a lactic acid bacterium may be appropriately modified if necessary, and used. That is, for example, sugars such as galactose, glucose, fructose, mannose, sorbose, mannitol, salicin, cellobiose, maltose, sucrose, trehalose, starch hydrolyzate and molasses may be used as carbon sources depending on their assimilability. For example, ammonium salts and ammonium nitrates such as ammonia, ammonium sulfate, ammonium chloride and ammonium nitrate may be used as nitrogen sources. For example, sodium chloride, potassium chloride, potassium phosphate, magnesium sulfate, calcium chloride, calcium nitrate, manganese chloride, ferrous sulfate and the like may be used as inorganic salts. In addition, organic components such as peptone, sake cake, whey, soybean powder, defatted soybean meal, meat extract and yeast extract may be used. In addition, for example, MRS medium or a modified medium thereof may be suitably used as an already prepared medium.

As the lactic acid bacterium, a culture obtained after the cultivation may be used as it is, or the obtained culture solution may be diluted or concentrated and used, or bacterial cells recovered from the culture may be used. In addition, as long as the effect of the present invention is not impaired, various additional operations such as heating and freeze-drying may also be performed after the cultivation. The additional operations are preferably those enabling a high survival rate of viable bacteria after performed. The lactic acid bacterium of the present invention may be viable or dead, and may include both viable and dead. The dead bacterium may be crushed.

3. Use of the Lactic Acid Bacterium of the Present Invention

Polysaccharides such as neutral and acidic polysaccharides which are produced by the lactic acid bacterium of the present invention as exopolysaccharides exhibit an activity of inhibiting hyaluronidase that is an enzyme hydrolyzing hyaluronic acid. The lactic acid bacterium of the present invention has an effect of reducing AST (aspartate aminotransferase) and the like, which are indications for investigating alcoholic damage, in serum of an alcoholic hepatitis-induced mouse model. The lactic acid bacterium of the present invention has a high resistance against gastric acid and bile acid. In addition, since the lactic acid bacterium of the present invention exerts a strong proliferation ability even in a medium using egg white, it has a strong defense mechanism against lysozyme degrading bacterial cell wall and transferrin interfering the iron utilization of bacteria by their chelating action, which are enzymes present in egg white.

As described above, the lactic acid bacterium of the present invention exerts various biological activities and has various physiological characteristics, and can be therefore widely used as an active ingredient in various compositions including a food and drink composition, a pharmaceutical composition, a feed composition and a cosmetic composition. For example, it can be used as an active ingredient of a food and drink composition, a pharmaceutical composition or a feed composition which are each used for hyaluronidase inhibition, antiallergy or anti-alcoholic damage. In addition, the lactic acid bacterium of the present invention can also be used as an active ingredient of a cosmetic composition together with egg white and the like.

The pharmaceutical composition of the present invention is not particularly limited as long as it contains the lactic acid bacterium of the present invention. The pharmaceutical composition of the present invention is usually used by blending the lactic acid bacterium of the present invention with a physiologically acceptable liquid or solid pharmaceutical carrier, followed by formulation.

The dosage form of the pharmaceutical composition of the present invention is not particularly limited, but specific examples of the dosage form include tablets, pills, powders, solutions, suspensions, emulsions, granules, capsules, syrups, suppositories, injections, ointments, patches, eye drops, and nose drops. In the formulation, additives, such as excipients, binders, disintegrants, lubricants, stabilizers, flavoring agents, diluents, surfactants, and solvents for injections, commonly used as pharmaceutical carriers may be used.

The content of the lactic acid bacterium in the pharmaceutical composition of the present invention may be appropriately determined depending on the dosage form, the dosage regimen, the age and sex of a subject, the kind of disease, the degree of disease, other conditions and the like, but is usually preferably in the range of $1\times10^6$ to $1\times10^{12}$ cfu/g or $1\times10^6$ to $1\times10^{12}$ cfu/ml, and more preferably in the range of $1\times10^7$ to $1\times10^{11}$ cfu/g or $1\times10^7$ to $1\times10^{11}$ cfu/ml. In the case where the lactic acid bacterium is dead, cfu/g or cfu/ml can be replaced with the number of cells per g or the number of cells per ml.

As long as the effect of the present invention is not impaired, the lactic acid bacterium of the present invention may be appropriately used in combination with other active ingredient, for example, an immunostimulant.

The administration timing of the pharmaceutical composition of the present invention is not particularly limited, but may be appropriately chosen according to a subject to be applied. The pharmaceutical composition of the present invention may also be administered prophylactically or used for a maintenance therapy. The administration mode may be preferably appropriately determined according to the dosage form, age, sex and other conditions of the administered subject, the degree of symptoms of the administered subject, and the like. In any case, the pharmaceutical composition of the present invention may be administered once per day or administered dividedly into a plurality of times, or administered once every several days or weeks.

The pharmaceutical composition of the present invention may be used, for example, to lower the allergy of a subject to be administered. In addition, the pharmaceutical composition of the present invention may be used for the treatment, alleviation or prevention of, for example, alcoholic liver damage, alcohol dependence, alcoholic hepatitis, fatty liver and the like.

The food and drink of the food and drink composition containing the lactic acid bacteria of the present invention are not particularly limited as long as they contain the lactic acid bacterium, but examples of the food and drink include beverages such as soft drinks, carbonated drinks, nutritional drinks, fruit juice beverages, and lactic acid bacteria beverages, concentrated stock solutions of these beverages, powders for the preparation of these beverages, and the like; ice cream, sherbet and ice confectionery such as shaved ice; confectioneries such as candy, gummy, cereal, chewing gum, candy, gum, chocolate, tablet candy, snack, biscuit, jelly, jam, cream, and baked confectionery; dairy products such as processed milk, milk drink, fermented milk, drink yogurt, and butter; bread; enteral nutritious food, liquid food, childcare milk, sports drink; food such as puree; and other functional foods. In addition, the food and drink may be supplements, and the supplements may be in the form of, for example, granules, powders, or tablets. In the case of supplements, the lactic acid bacterium may be ingested without being affected by other foods with respect to the amount of meal and calorie intake per day.

The food and drink as described above may be prepared by adding the lactic acid bacteria to raw materials of food and drink, or prepared in the same manner as usual food and drink. The addition of the lactic acid bacteria may be performed at any stage of the process of preparing the food and drink. The food and drink may be prepared after a fermentation process of the added lactic acid bacteria. Examples of such food and drink include fermented foods such as lactic acid bacterium beverages and fermented milks.

As raw materials for the food and drink, raw materials used for usual foods and drinks may be used. The prepared food and drink may be ingested orally.

The food and drink of the present invention also include raw materials for preparing the food and drink, and food additives or the like added to the food and drink during the preparation processes or after the preparation processes. For example, the lactic acid bacterium of the present invention may be used as a starter for preparing fermented milks. In addition, the lactic acid bacterium of the present invention may be added to the fermented milks after prepared.

The content of the lactic acid bacterium in the food and drink composition of the present invention may be appropriately determined depending on the embodiment of the food and drink, but is usually preferably in the range of $1\times10^6$ to $1\times10^{12}$ cfu/g or $1\times10^6$ to $1\times10^{12}$ cfu/ml, and more preferably in the range of $1\times10^7$ to $1\times10^{11}$ cfu/g or $1\times10^7$ to $1\times10^{11}$ cfu/ml. In the case where the lactic acid bacterium is dead, cfu/g or cfu/ml can be replaced with the number of cells per g or the number of cells per ml.

The food and drink composition containing the lactic acid bacterium of the present invention can be used in various uses utilizing the antiallergy effect or anti-alcoholic damage effect.

The food and drink containing the lactic acid bacterium of the present invention may be manufactured and sold as a food and drink showing its use. Such a food and drink may be showed by "for allergy improvement", "for alcoholic damage improvement", and the like. Other showing may also be used, needless to say, as long as it indicates the secondary effect caused by such improvement effect. The term "show" as used herein means all actions for informing a consumer of the aforementioned use, and any actions fall under the showing, regardless of the purpose and content of the showing, a subject and medium to be showed, and the like, as long as they recall or infer the aforementioned use. However, the showing is preferably made by an expression such that a consumer can directly recognize the aforementioned use.

Specifically, it may be exemplified that the aforementioned use is showed on a commodity or a package thereof regarding the food and drink of the present invention. In particular, the use is preferably showed on advertisement materials at sales sites and other documents, such as packages, containers, catalogs, pamphlets and POPs. Examples of the showed commodities include health foods, functional foods, enteral nutrition foods, special use foods, nutritional functional foods, quasi drugs, and special health foods.

Examples of the feed of a feed composition containing the lactic acid bacterium of the present invention include pet food, livestock feed and fish feed. Such a feed may be prepared by mixing common feed, for example, cereals, cakes, brans, fish meals, bone meals, oils and fats, skim milk powders, wheys, bitterns, mineral feeds, yeasts, and the like with the lactic acid bacterium. In addition, for example, likewise the case of silage, a feed may be prepared through a fermentation process with the lactic acid bacterium added thereto. The prepared feed may be orally administered to general mammals, livestock, farmed fishes, pet animals and the like. In the case of farmed fishes, it may be adopted to spread fermented products, to which the lactic acid bacterium of the present invention is added, to the farmed place of fishes.

The content of the lactic acid bacterium in the feed composition of the present invention may be appropriately determined depending on the embodiment of the feed or the administered subject, but is usually preferably in the range of $1\times10^6$ to $1\times10^{12}$ cfu/g or $1\times10^6$ to $1\times10^{12}$ cfu/ml, and more preferably in the range of $1\times10^7$ to $1\times10^{11}$ cfu/g or $1\times10^7$ to $1\times10^{11}$ cfu/ml. In the case where the lactic acid bacterium is dead, cfu/g or cfu/ml can be replaced with the number of cells per g or the number of cells per ml.

The feed composition containing the lactic acid bacterium of the present invention can be used in various uses utilizing, for example, the antiallergy effect.

Examples of the cosmetic product of the cosmetic composition containing the lactic acid bacterium of the present invention include washing agents such as soaps, body shampoos, cleansing creams and facial cleansers; creams such as lotions, vanishing creams, cold creams, emollient creams and massage creams; milky lotions and serums.

In the cosmetic composition containing the lactic acid bacterium of the present invention, it is preferable to use, for example, a lactic acid-fermented egg white obtained by adding the lactic acid bacterium of the present invention to a liquid egg white prepared by breaking eggs of birds such as chickens and removing the egg yolk, followed by the fermentation. In general, such lactic acid fermentation is preferably performed by using glucose or the like as a nutrient source, adding a fermentation promoting substance such as yeast extract, if necessary, and fermenting them. The form of the lactic acid-fermented egg white may be, for example, liquid, powder, cream, paste or jelly, depending on the cosmetic to be blended therewith.

The content of the lactic acid bacterium in the cosmetic composition of the present invention is, for example, usually 0.001% or more by weight, preferably 0.01% or more by weight, in terms of the dried matters of the lactic acid-fermented egg white.

The cosmetic composition containing the lactic acid bacterium of the present invention can be used in various uses utilizing, for example, the antiallergy effect. It can also be used as a cosmetic product exhibiting a whitening effect or a moisturizing effect.

EXAMPLES

Hereinafter, the present invention will be described in more detail with reference to examples, but the present invention is not limited by these examples.

Example 1

Isolation and Identification of Lactic Acid Bacterium
1. Isolation of Lactic Acid Bacterium Sample The leaves, stems and fruits of a fig (variety "TOYO-MITSU HIME") were chosen and cut into pieces of 2 to 3 mm using sterilized tweezers and scissors. Every five to six pieces were then placed in a sterilized test tube containing MRS liquid medium, and statically cultured at 28° C. and 37° C. until the MRS medium as a standard medium for a lactic acid bacterium became turbid (proliferated). By the way, it took 2 to 4 days for the proliferation of the lactic acid bacterium candidate strains to be visible.

A part of each culture liquid of the lactic acid bacterium candidate strains was subjected to a line drawing paint on MRS agar medium using a disposable loop, followed by stationary culture. Among colonies formed on the agar medium, all of differently colored, lustrous and shaped colonies were picked up and subjected to a line drawing paint on a fresh MRS agar medium, and the colonies were purified.

$H_2O_2$ test was performed for each purified colony to verify the presence or absence of the production of a catalase enzyme. This is a test method for observing the presence or absence of oxygen generated when catalase is present, which is observed when cell bodies are exposed to 10% $H_2O_2$ solution. By the way, a lactic acid bacterium produces no catalase.

As a result of attempting the search and isolation from a fig, one lactic acid bacterium candidate strain showing catalase-negative was obtained from the leaves of a fig as the isolation source.

2. Identification of the Isolated Strain

The aforementioned lactic acid bacterium candidate strain was again cultured in MRS liquid medium, and the bacterial cell bodies were obtained by centrifugation. After the cell bodies were treated with cell wall lytic enzyme, a genomic DNA was extracted using DNAzol reagent.

According to the method as described in Lane, D J (1991), "16S/23S rRNA sequencing", Nucleic Acid Techniques in Bacterial Systematics, pp. 115-175, edited by E. Stackebrandt & M. Goodfellow. Chichester: Wiley, a genomic DNA PCR was performed using a genomic DNA as a template and using 27f primer (5'-AGAGTTTGATCCTGGCTCAG-3') (SEQ ID NO: 1 in Sequence Listing) and 1525r primer (5'-AAAGGAGGTGATCCAGCC-3') (SEQ ID NO: 2 in Sequence Listing), thereby to amplify 16S rDNA part. Then, an objective fragment was recovered from agarose gel according to NucleoSpin Gel and PCR Clean-up kit (manufactured by Mahalay Nagel). A sequencing reaction by a dye terminator method for sequencing a base sequence was performed with Big Dye Terminator Cycle Sequencing FS Ready Reaction Kit ver. 3.1 (manufactured by ThermoFisher Scientific), and analysis was made with ABI PRISM 3130 xl Genetic Analyzer (manufactured by ThermoFisher Scientific). The base sequence of the analyzed 16S rDNA had the base sequence of SEQ ID NO: 3 in Sequence Listing. The base sequence was subjected to a homology search by BLAST program and compared with the database of DNA data bank (DDBJ/EMBL/GenBank) to make a taxonomic identification on the isolated strain.

The lactic acid bacterium candidate strain isolated from leaves of a fig was named strain IJH-SONE68 and identified as *Lactobacillus paracasei* because it was 100% identical to a base sequence which was in the strain of *Lactobacillus paracasei* R094 already registered in DNA data bank (DDBJ/EMBL/GenBank) and which had NR-025880 as the accession number of the base sequence.

This strain was internationally deposited under the accession number of NITE P-02242 at Patent Microorganisms Depositary, National Institute of Technology and Evaluation (#122, 2-5-8 Kazusakamatari, Kisarazu-shi, Chiba 292-0818, Japan) on Apr. 19, 2016. The deposition was then transferred to an international deposit under the Budapest Treaty and given the international deposit accession number of NITE BP-02242 on May 26, 2017.

3. Sequence Analysis of Genomic DNA

The genomic DNA sequence from the strain IJH-SONE68 was sequenced by PacBio RS II (Pacific Biosciences, Menlo Park, Calif., USA) on a single molecule real-time (SMRT) cell using P6 polymerase and C4 chemistry (P6C4). The purified genomic DNA sample was sheared into fragments using g-TUBE Kit (Covaris, Woburn, Mass., USA). The sheared fragments were then purified using AMPure PB Kit (Pacific Biosciences). DNA library was constructed using PacBio DNA Template Prep Kit 1.0 (Pacific Biosciences) and PacBio DNA/Polymerase Binding Kit P6 (Pacific Biosciences). The short fragments were removed using Blue Pippin (Sage Science, Beverly, Mass., USA), and the purified DNA library was then sequenced on PacBio SMRT Platform. De novo assembly was performed according to the protocol of Hierarchical Genome Assembly Process (HGAP) (Nat. Methods, 10, 563-56933), and the obtained whole genome contig was annotated by Microbial Genome Annotation Pipeline (MiGAP) (The 20th International Conference on Genome Informatics (GIW2009) Poster and Software Demonstrations (Yokohama), S001-1-2).

4. Results of the Sequence Analysis of the Genomic DNA

The whole genome sequence of the strain IJH-SONE68 was sequenced and, as a result, the genomic DNA consisted of 3,084,917 bp with a GC content of 46.37%, and the number of structural genes was predicted to be 2,963 according to MiGAP. Furthermore, it was shown from the results that the strain IJH-SONE68 harbored two plasmids, one of which had a size of at least 51 kb, and the other had a size of 45,267 bp. The strain IJH-SONE68 had a larger genome size and the larger number of structural genes, as compared with other lactic acid bacteria.

Example 2

Mycological Properties of Separated and Identified Lactic Acid Bacterium

The aforementioned isolated and identified lactic acid bacterium strain IJH-SONE68 was a catalase-negative, gram-positive rod and had a white colony forming property, as shown in the photograph of FIG. 1, and further had the characteristic of conditional hetero-lactic acid fermentation and the ability of producing polysaccharides.

Example 3

Saccharide Assimilation Ability of the Isolated and Identified Lactic Acid Bacterium 1. Test Method of Assimilation Ability The strain IJH-SONE68 was investigated for the assimilation ability of 49 kinds of saccharides according to the following test method.

The strain IJH-SONE68 was statically cultured in MRS liquid medium until the proliferation stationary phase. The bacterial cell bodies obtained by centrifugation were washed with an appropriate amount of a suspension medium (manufactured by BioMeieux), and finally suspended in 2 mL of a suspension medium. A portion of the resultant suspension was added to 5 mL of a suspension medium to determine an amount (n) for McFarland turbidity to become 2. Subsequently, 2n of a bacterial solution was added to API 50 CHL medium (manufactured by BioMerieux), and this solution was dispended to each well of API 50 CHL kit (manufactured by BioMerieux, 49 kinds of saccharides were coated on the bottom of each well). Finally, mineral oil was overlaid and set in a tray containing a sterilized water. After culturing at 37° C. for 48 hours, the presence or absence of the assimilation ability was assessed by observing the change in color tone in each well.

2. Test Results of the Assimilation Ability

Table 1 shows the results of investigating the assimilation ability of the strain IJH-SONE68 against 49 kinds of saccharides. Table 1 also shows the results of investigating the assimilation ability of other *Lactobacillus paracasei* strains described in patent-laid open publications using similar kits.

TABLE 1

Assimilation abilities of the strain IJH-SONE68 against saccharides

| Substrates | IJH-SONE 68 NITE BP-02242 | JP2016-123382 NITE P-01960 | JP2007-189973 NLB162 NITE P-159 | JP2007-189973 NLB163 NITE P-160 | JP2016-113378 MCC1849 NITE BP-01633 | JP2016-37451 HL190 NITE P-01810 | JP2011-142907 LT12 NRRL-B50327 |
|---|---|---|---|---|---|---|---|
| control | − | − | − | − | − | − | − |
| glycerol | − | − | − | − | − | − | − |
| erythritol | − | − | − | − | − | − | − |
| D-arabinose | − | − | − | − | − | − | − |
| L-arabinose | − | − | − | − | − | − | − |
| D-ribose | + | + | + | + | + | + | + |
| D-xylose | − | − | − | − | − | − | − |
| L-xylose | − | − | − | − | − | − | − |
| D-adonitol | + | − | − | − | − | − | − |
| methyl-βD-xylopyranoside | − | − | − | − | − | − | − |
| D-galactose | + | + | + | + | + | + | + |

TABLE 1-continued

Assimilation abilities of the strain IJH-SONE68 against saccharides

| Substrates | IJH-SONE 68 NITE BP-02242 | JP2016-123382 NITE P-01960 | JP2007-189973 NLB162 NITE P-159 | JP2007-189973 NLB163 NITE P-160 | JP2016-113378 MCC1849 NITE BP-01633 | JP2016-37451 HL190 NITE P-01810 | JP2011-142907 LT12 NRRL-B50327 |
|---|---|---|---|---|---|---|---|
| D-glucose | + | + | + | + | + | + | + |
| D-fructose | + | + | + | + | + | + | + |
| D-mannose | + | + | + | + | + | + | + |
| L-sorbose | + | − | + | + | − | − | + |
| L-rhamnose | − | + | − | − | − | − | − |
| dulcitol | − | − | − | − | − | − | + |
| inositol | − | − | − | − | − | − | + |
| D-mannitol | + | + | + | + | + | − | + |
| D-sorbitol | − | + | + | − | + | − | + |
| methyl-αD-mannopyranoside | − | − | + | − | − | − | − |
| methyl-αD-glucopyranoside | − | − | ± | + | ± | − | + |
| N-acetylglucosamine | + | + | + | + | ± | + | + |
| amygdalin | − | + | + | + | ± | + | + |
| arbutin | − | + | + | + | + | + | + |
| esculin + ferric citrate | + | + | ± | ± | + | + | + |
| Salicin | + | + | + | + | + | + | + |
| D-cellobiose | + | + | + | + | + | + | + |
| D-maltose | + | + | + | + | + | + | + |
| D-lactose | − | + | − | + | + | + | + |
| D-melibiose | − | − | − | − | − | − | − |
| D-sucrose | + | + | + | + | + | + | + |
| D - trehalose | + | + | + | + | + | + | + |
| Inulin | − | + | − | − | + | + | + |
| D-melezitose | + | + | + | + | + | − | + |
| D-raffinose | − | − | − | − | − | − | − |
| Starch | − | − | − | − | − | − | − |
| glycogen | − | − | − | − | − | − | − |
| Xylitol | − | − | − | − | − | − | − |
| gentibiose | + | + | + | + | ± | + | + |
| D-turranose | − | + | + | + | + | + | + |
| D-lyxose | − | − | ± | − | − | − | + |
| D-tagatose | + | + | + | + | + | + | + |
| D-fucose | − | − | − | − | − | − | − |
| L-fucose | − | − | − | − | − | − | − |
| D-arabitol | − | − | − | − | − | − | − |
| L-arabitol | − | − | − | − | − | − | − |
| gluconic acid | + | + | ± | ± | ± | + | + |
| 2-ketogluconic acid | − | − | − | − | − | − | − |
| 5-ketogluconic acid | − | − | − | − | − | − | − |

In Table 1, + indicates the possession of assimilation ability, and − indicates no possession of assimilation ability.

Saccharide assimilation kit: Ap150CHL (manufactured by bioMerieux) was used in JP2016-123382 and JP2011-142907, AIP50CH (manufactured by Simex•BioMerieux) was used in JP2016-113378, and there are no descriptions for kits used in JP2007-189973 and JP2016-37451.
NITE P-01960, NITE PB-01633 and NRRL-B50327 are *Lactobacillus paracasei*, and NITE P-159, NITE P-160 and NITE P-01810 are *Lactobacillus paracasei* ssp. *paracasei*.

As can be seen from the results of Table 1, when compared with other *Lactobacillus paracasei* strains, the strain IJH-SONE68 cannot assimilate amygdalin that may generate hydrocyanic acid when decomposed, or arbutin that is reported to inhibit melanin production thereby to exert a whitening effect, and thus decomposes neither amygdalin nor arbutin. Hence, the strain IJH-SONE68 can be said to be excellent in the safety, and also excellent in the whitening effect when used as an additive for cosmetics. In addition, while other *Lactobacillus paracasei* strains cannot assimilate D-adonitol, but can assimilate D-chulanose, the strain IJH-SONE68 has the characteristics of being able to assimilate D-adonitol, but unable to assimilate D-chulanose.

Example 4

1. Isolation and Purification of Exopolysaccharides Produced by the Strain IJH-SONE68

Exopolysaccharides produced by the strain IJH-SONE68 were isolated and purified according to the following method.

The strain IJH-SONE68 was statically cultured in MRS liquid medium until the proliferation stationary phase. 5 mL of the resultant culture solution was used as a seed culture solution, and inoculated on 5 L of a semisynthetic medium for producing exopolysaccharides (the composition thereof will be described below), followed by static culture at 37° C. for 120 hours. After the resultant culture solution was cooled to 4° C., proteins contained in the culture supernatant were denatured, and 202.5 mL of a 100% trichloroacetic acid aqueous solution was added thereto, mixed and allowed to stand for 30 minutes to remove them as precipitates in a later step. After the precipitates were removed by centrifugation, an equal amount of acetone was added to the collected supernatant and mixed, and the resultant mixture was allowed to stand at 4° C. overnight to precipitate polysaccharides produced by the strain IJH-SONE68. The precipitates were collected by centrifugation, and the resultant precipitates were then washed with 250 mL of 70% ethanol. After the precipitates were air-dried, 75 mL of 50 mM Tris-HCl buffer (pH 8.0) was added to the resultant precipitates, and mixed for 1 hour to dissolve the precipitates. After insoluble impurities were removed by centrifugation to recover a supernatant, 750 µL of 1 mg/mL DNase solution (Worthington, Inc.) and 750 µL of 1 mg/mL RNase solution (Nacalai Tesque, Inc.) were each added to the recovered supernatant, followed by being allowed to react at 37° C. for 8 hours. Subsequently, 750 µL of 2 mg/mL proteinase K solution (manufactured by Wako Pure Chemical Industries, Ltd.) was added, and the resultant mixture was reacted at 37° C. for 16 hours. The resultant solution after the reaction was cooled to 4° C., the added enzymes were each denatured, and 8.75 mL of a 100% trichloroacetic acid aqueous solution was then added thereto, mixed and allowed to stand for 1 hour to remove the enzymes as precipitates in the next centrifugation. The resultant precipitates were removed by centrifugation to obtain a supernatant, 262.5 mL of 100% ethanol was added to the obtained supernatant, the resultant mixture was thoroughly mixed, and the polysaccharides produced by the strain IJH-SONE68 strain were then recovered as precipitates by centrifugation. After the precipitates were washed with 50 mL of 70% ethanol, the precipitates were air-dried, an appropriate amount (about 25 mL) of a purified water was added thereto, and the resultant mixture was allowed to stand overnight at 4° C. to dissolve the polysaccharides. For the polysaccharides sample after the dissolution, small molecules such as monosaccharides in the recovered sample were removed using an ultrafiltration unit (Merck Ltd.) of 10,000 MWCO while replacing the solvent with a purified water, and a purified polysaccharide sample was thus obtained.

The purified polysaccharide sample was applied to an open column (2.5×22 cm) packed with TOYOPEARL DEAE-650M resin (Tosoh Corporation) previously equilibrated with 50 mM Tris-HCl buffer (pH 8.0), and column work was performed to isolate and purify the sample to neutral polysaccharide fractions and acidic polysaccharide fractions. The same buffer was used as an elution solution, and a flow rate was fixed at 1 mL/min. In addition, eluates were collected in different test tubes at every 6 mL. First, from the beginning to 240 minutes, elution was made with the same buffer (Test Tube Nos. 1 to 40). Next, from 240 minutes to 600 minutes, a concentration gradient of 0 to 500 mM NaCl was prepared using the same buffer, and elution was continued with the gradient (Test Tube Nos. 41 to 100). The column isolation spectrum is illustrated in FIG. 2. After the presence of polysaccharides was confirmed by a phenol sulfuric acid method (described below) for all the samples eluted in the test tubes, the confirmed solutions in the test tubes were collected as neutral polysaccharide fractions and acidic polysaccharide fraction, respectively. For each fraction, an ultrafiltration unit of 10,000 MWCO was used to remove small molecules such as monosaccharides in the recovered sample while replacing the solvent with purified water.

As a result, neutral polysaccharide fractions and acidic polysaccharide fractions were isolated and purified as exopolysaccharides produced by the strain IJH-SONE68.

A semisynthetic medium for producing polysaccharides was prepared by modifying a medium described in Kimmel S A, Roberts R F., "Development of a growth medium suitable for exopolysaccharide production by *Lactobacillus delbrueckii* ssp. *Bulgaricus* RR.", Int. J. Food Microbiol., 40, 87-92 (1998), as follows:

| Semisynthetic medium for producing polysaccharides | [g/L] |
| --- | --- |
| Glucose | 20 |
| Tween 80 | 1.0 |
| Ammonium citrate | 2.0 |
| Sodium acetate | 5.0 |
| $MgSO_4 \cdot 7H_2O$ | 0.1 |
| $MnSO_4 \cdot 5H_2O$ | 0.05 |
| $K_2HPO_4$ | 2.0 |
| Bacto casitone | 10.0 |
| Vitamin Soln. | 2 mL |
| Trace element Soln. | 1 mL |

| Vitamin Soln. | [g/L] |
| --- | --- |
| 4-Aminobenzoic acid | 0.05 |
| Biotin | 0.001 |
| Folic acid | 0.025 |
| Lipoic acid | 0.025 |
| Nicotinic acid | 0.1 |
| Pantothenic acid | 0.05 |
| Pyridoxamin-HCl | 0.25 |
| Vitamin $B_{12}$ | 0.05 |
| Pyridoxine | 0.025 |
| Riboflavin | 0.05 |
| Thiamine | 0.1 |

Trace element Soln. is described in Kets E P W, Galinski E A, de Bont J A M. Carnitine: "A novel compatible solute in *Lactobacillus plantarum*", Arch. Microbiol., 192, 243-248 (1994), and the composition is as follows:

| Trace element Soln. | [g/L] |
| --- | --- |
| 25% HCl | 10 mL |
| $FeCl_2 \cdot 4H_2O$ | 1.5 |
| $CoCl_2 \cdot 6H_2O$ | 0.19 |
| $MnCl_2 \cdot 4H_2O$ | 0.1 |
| $ZnCl_2$ | 0.07 |
| $H_3BO_3$ | 0.006 |
| $Na_2MoO_4 \cdot 2H_2O$ | 0.036 |
| $NiCl_2 \cdot 6H_2O$ | 0.024 |
| $CuCl_2 \cdot 2H_2O$ | 0.002 |

Phenol sulfuric acid method (DuBois M, Gilles K A, Hamilton J K, Rebers P A, Smith F., "Colorimetric method for determination of sugars and related substances", Anal. Chem., 28, 350-356 (1956))

30 µL of a subject sample was mixed with an equal amount of 5 w/v % phenol aqueous solution, and 150 µL of a concentrated sulfuric acid was added to the resultant mixture and mixed with each other to allow a reaction to start. Immediately after 10 minutes, the reaction solution was cooled by ice to stop the reaction. The concentration of saccharides was obtained by measuring the absorbance of the reaction solution at 490 nm. The concentration was determined using a calibration curve prepared by performing the same experiment using glucose as a standard.

2. Analysis of Exopolysaccharides

Figure 4:
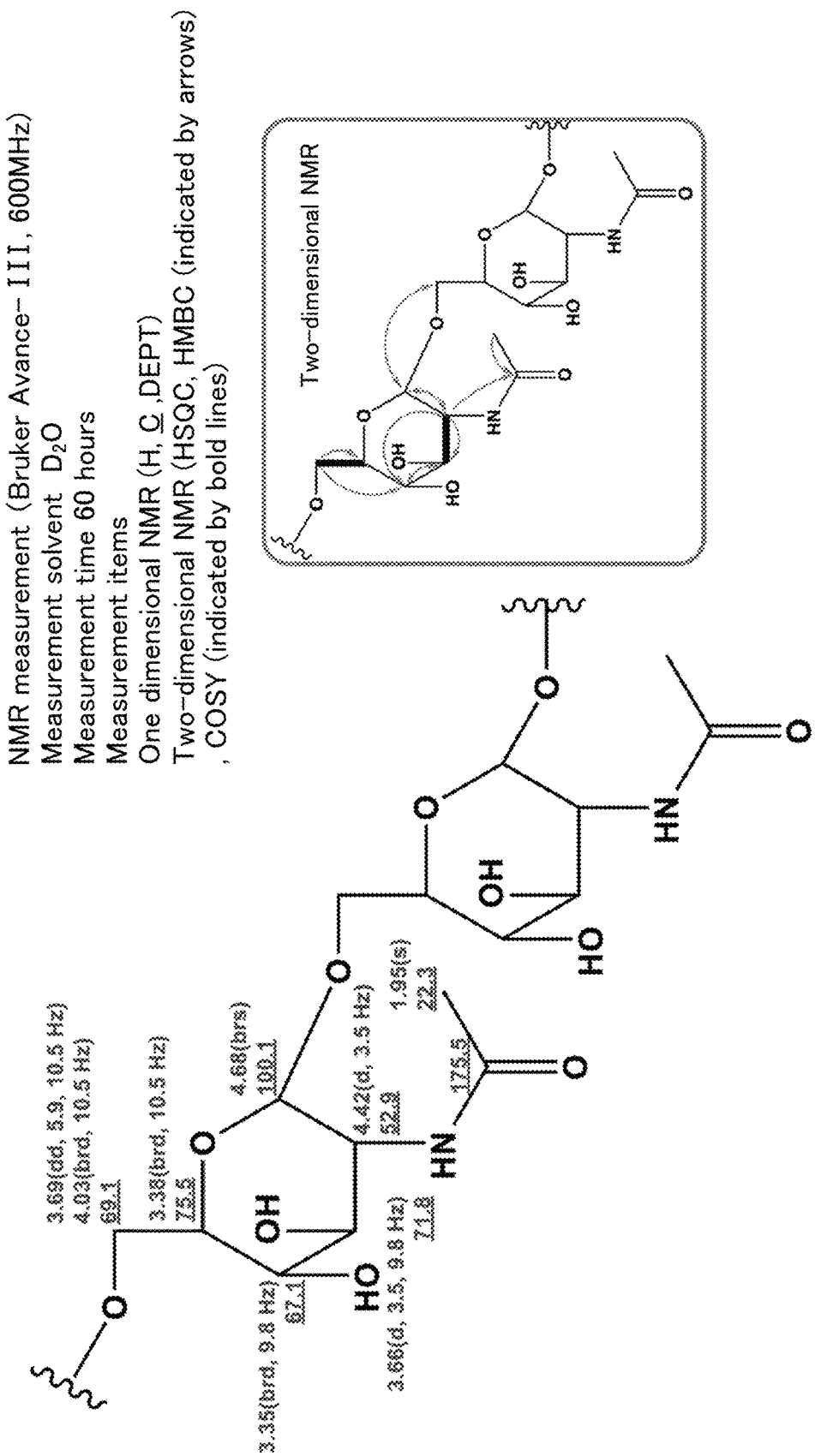
FIG. 4 illustrates results of structurally analyzing a neutral exopolysaccharide on the basis of the NMR profile. These structural analysis results revealed that the neutral exopolysaccharide of *Lactobacillus paracasei* strain IJH-SONE68 has a structure in which N-acetylglucosamines are linked with each other via $\alpha$-1,6 bond.

The neutral exopolysaccharide purified by the aforementioned anion exchange column chromatography (TOYOPE- ARL DEAE-650 M resin (Tosoh Corporation)) was subjected to proton-NMR and carbon-NMR, and the obtained NMR profiles are each illustrated in FIG. 3. The structural analysis results of the neutral exopolysaccharide from these NMR profiles are illustrated in FIG. 4.

From the structural analysis results, it was revealed that the neutral exopolysaccharide produced by the strain IJH-SONE68 has a structure in which N-acetylglucosamines are linked with each other via α-1,6 bond.

3. Analysis of Exopolysaccharide-Biosynthesizing Gene Cluster of the Strain

IJH-SONE68

Figure 5:
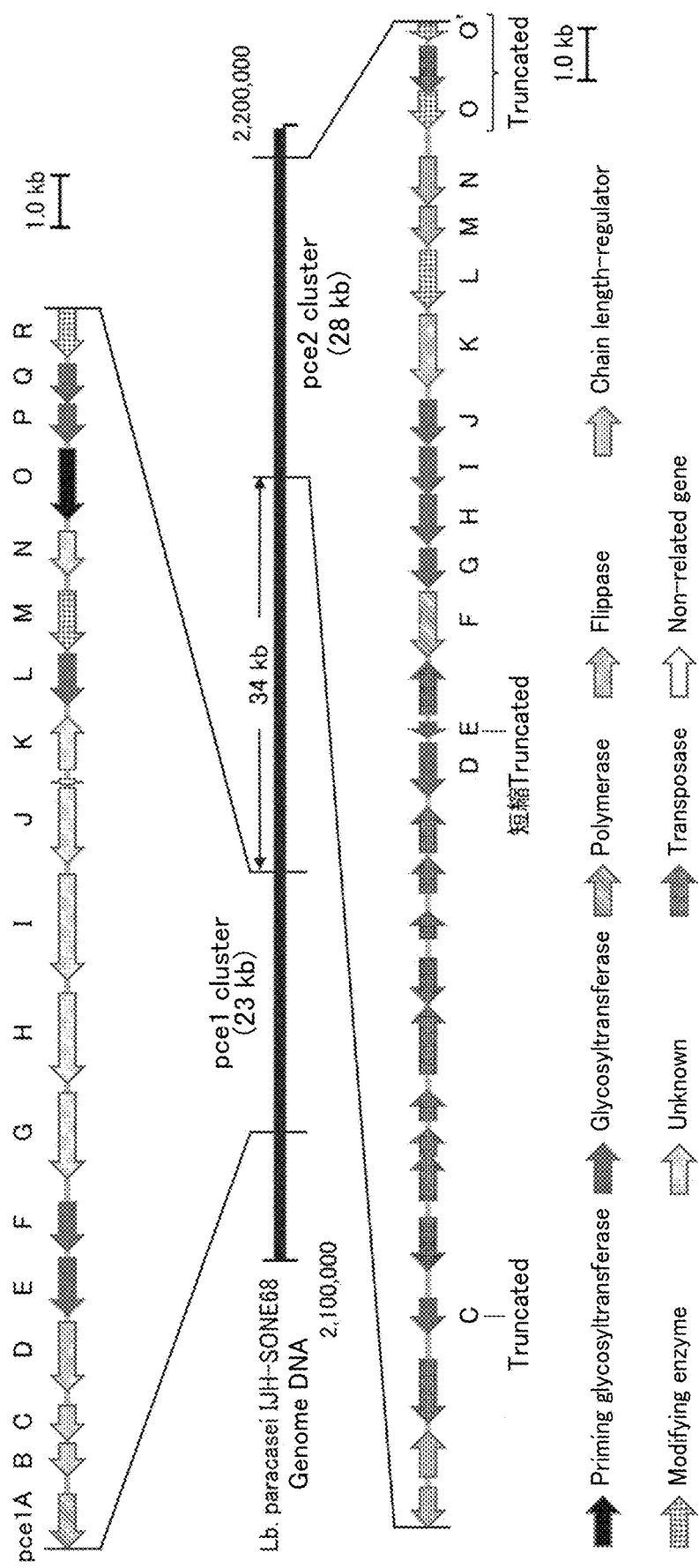
FIG. 5 is a structural diagram of exopolysaccharide biosynthetic gene clusters, which are named pce1 cluster and pce2 cluster, of genomic DNA of *Lactobacillus paracasei* strain IJH-SONE68.

Based on the annotation of the genome sequence of the strain IJH-SONE68 as described in Example 1, two exopolysaccharide-biosynthesizing gene clusters were found in the genomic DNA (FIG. 5). A gene cluster, which is one of the two clusters and which is 23 kb cluster, was named pce1 cluster, and the pce1 cluster was composed of 18 open reading frames (ORFs) (pce1A to R) including unknown protein-encoding genes. The other gene cluster of 28 kb was named pce2, and the pce2 cluster included 12 complete ORFs and three truncated ORFs (pce2A to O). Furthermore, 12 transposase-related genes were found in the pce2 cluster.

With respect to genes encoding proteins necessary for the biosynthesis of exopolysaccharides, wzb gene encoding protein-tyrosine phosphatase Wzb that acts as a chain-length factor (Yother J. Annu. Rev. Microbiol., 65, 563-581 (2011)) was not found in the pce1 cluster. On the other hand, a gene having a homology with priming glycosyltransferase that catalyzes the first step of saccharide polymerization (van Kranenburg R, Vos H R, van Swam I I, Kleebezem M, de Vos W M., J. Bacteriol., 1999 October; 181(20): 6347-6353) was not present in the pce2 cluster.

Figure 6:
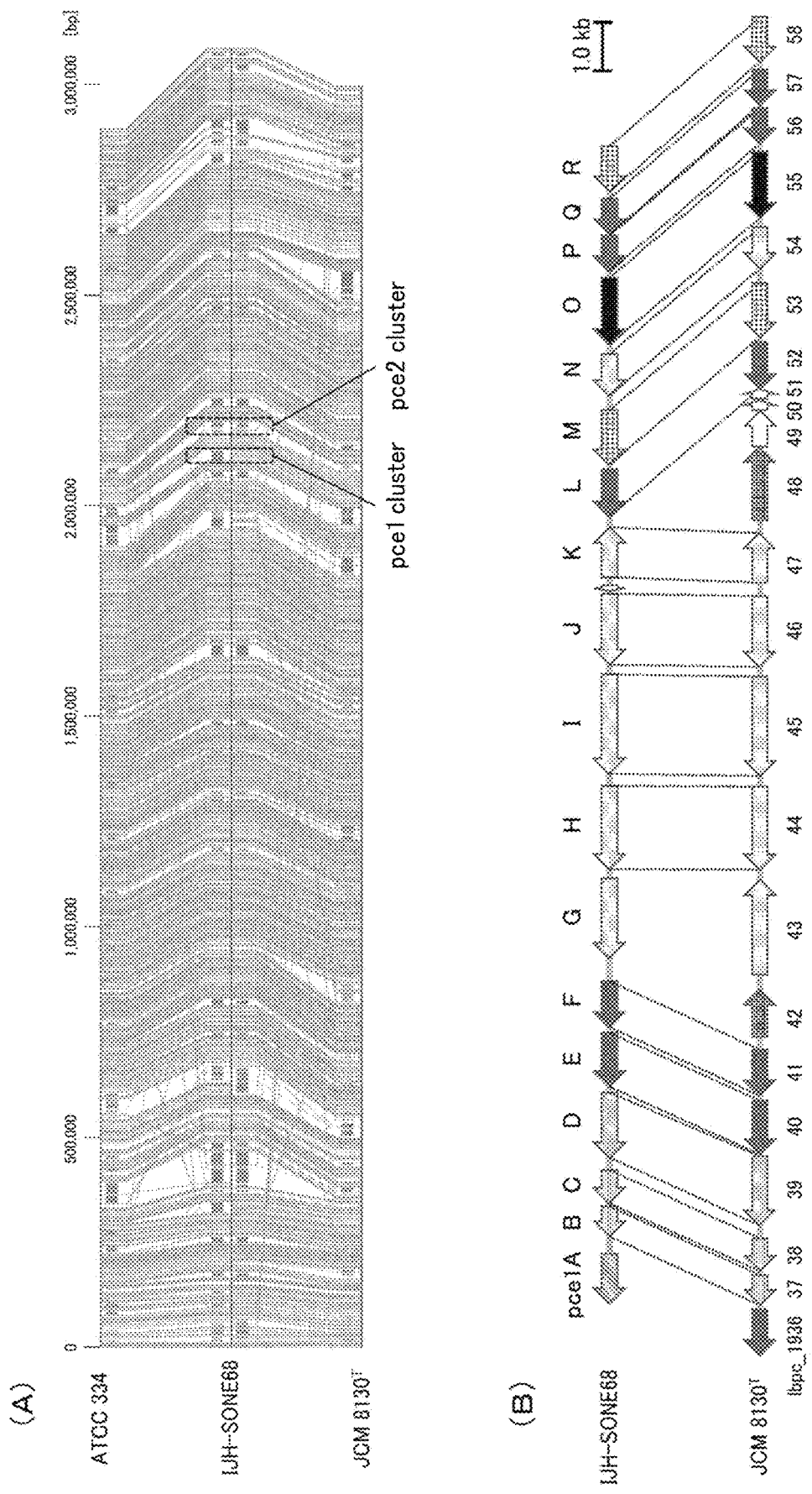
FIG. 6 illustrates at (A) genome rearrangement maps among three lactic acid bacteria of *Lactobacillus paracasei* strain IJH-SONE68, strain ATCC334, and strain JCM8130T.

The genome rearrangement map among three lactic acid bacteria of the strains IJH-SONE68, ATCC 334 (Makarova, K. et. al, Proc. Natl. Acad. Sci. U.S.A., 103 (42), 15611-15616 (2006)) and JCM 8130T (Toh, H. et. al, PLoS ONE 8, e75073 (2013)) was drawn up (FIG. 6). From the map, it was revealed that the pce2 cluster region is specific for the strain IJH-SONE68. On the other hand, a gene cluster homologous to pce1 cluster was not observed in the strain ATCC 334, but was present in the strain JCM 8130T.

Based on the aforementioned homology search, genes that were each homologous with wzb gene and priming glycosyltransferase gene were observed in the pce1 and pce2 clusters. Since other clusters or the like were not found in the genomic DNA of the strain IJH-SONE68, genes necessary for the biosynthesis of exopolysaccharides were considered to be complemented with the pce1 and pce2 clusters. In fact, the pce1 cluster and the pce2 cluster were only 34 kb apart from each other.

In the pce2 cluster, a protein deduced from one of glycosyltransferase genes, named pce2J, was found to have a motif or domain similar to pfam02485 motif or domain found in already known β-1,6-acetylglucosaminyltransferase (Genes Dev. 1993 March; 7(3):468-478, and J. Biol. Chem., 1999 Jan. 29; 274(5):3215-3221), and this structural gene was suggested to be involved in the biosynthesis of the neutral exopolysaccharide. Indeed, the pce2 cluster was specific for the strain IJH-SONE68 as compared with the strains ATCC 334 and JCM 8130T, and a neutral polysaccharide having a new structure was considered to be biosynthesized from the pce2 cluster.

Example 5

Hyaluronidase Activity Inhibition of Exopolysaccharides Produced by the Strain IJH-SONE68

A hyaluronidase activity inhibition was investigated on the polysaccharide sample containing the neutral polysaccharide fractions and the acidic polysaccharide fractions, the neutral polysaccharide fractions, and the acidic polysaccharide fractions, which were exopolysaccharides produced by the strain IJH-SONE68 and obtained in Example 4.

1. Test Method

5 μL of a hyaluronidase enzyme solution (MP Biomedicals, 4 mg/mL, 100 mM sodium acetate buffer (pH 4.0)) was added to 10 μL of an aqueous solution containing polysaccharides at an optional concentration, which was prepared from the polysaccharide sample containing the neutral polysaccharide fractions and the acidic polysaccharide fractions, the neutral polysaccharide fractions, and the acidic polysaccharide fractions, which were exopolysaccharides produced by the strain IJH-SONE68 and obtained in Example 4. The resultant mixture was incubated at 37° C. for 20 minutes. Thereafter, to the mixture, 10 μL of an enzyme-activating solution (0.5 mg/ml Compound 48/80 (manufactured by MP Biomedicals)), 3.75 mg $CaCl_2 \cdot 2H_2O$, and 100 mM sodium acetate buffer (pH 4.0)) were added, and incubated again at 37° C. for 20 minutes. Subsequently, to the resultant mixture, 25 μL of a sodium hyaluronate solution (Wako Pure Chemical Industries, 0.8 mg/mL, 100 mM sodium acetate buffer (pH 4.0)) was added, and further reacted at 37° C. for 40 minutes. After the reaction, the reaction was terminated by adding 10 μL of 0.4 M NaOH aqueous solution. Subsequently, to the reaction solution, 10 μL of 100 mM potassium borate buffer (pH 10.0) was added, and the mixture was heated at 100° C. for 3 minutes, and immediately thereafter cooled with ice. 40 μL of the reaction solution was mixed with 200 μL of p-DMAB solution (described below), the mixture was reacted at 37° C. for 20 minutes, and the absorbance at 585 nm was then measured. As a control, a reaction solution not containing a hyaluronidase enzyme solution was prepared and experimented in the same manner.

The inhibition rate of the enzyme activity for the polysaccharide sample was obtained from the following equation:

Inhibition rate(%)=100−(S/C)×100

In this equation, C means the enzyme activity in the absence of the sample, and S means the enzyme activity in the presence of the sample. In addition, $IC_{50}$ value of the polysaccharide sample was obtained by obtaining a plurality of data on the changed content concentrations, plotting these data on X-axis as the concentration of the polysaccharide sample, and on Y-axis as the inhibition percentage, and obtaining the value from the following approximation equation:

$$Y=\alpha/(1+\beta e^{-\gamma X}) \qquad \text{[Equation 1]}$$

In the equation, α, β and γ are given constants.

p-DMAB solution (Fujitani N, Sakai S, Yamaguchi Y, Takenaka H, "Inhibitory effects of microalgae on the activation of hyaluronidase", J. Appl. Phycol., 13, 489-492 (2001))

The p-DMAB solution was prepared by diluting 10× stock solution (5 g of p-dimethylaminobenzaldehyde, 6 ml of 10 M HCl, 44 ml of acetic acid) with acetic acid immediately prior to use.

2. Test Results

Table 2 shows the obtained results of the inhibition on hyaluronidase activity.

TABLE 2

Hyaluronidase activity inhibition of exopolysaccharides produced by the strain IJH-SONE68

| Tested samples | $IC_{50}$ (µg/ml) |
|---|---|
| Polysaccharide sample of IJH-SONE68 (containing neutral and acidic polysaccharide fractions) | 370 |
| Neutral polysaccharide fractions of IJH-SONE68 | 550 |
| Acidic polysaccharide fractions of IJH-SONE68 | 1200 |
| Fucoidan (Laminaria Japonic) | 2000<* |
| Ketotifen fumarate | 2000<* |
| Dipotassium glycyrrhizinate | 530 |

*Hyaluronidase activity inhibition was not observed until the concentration of 2000 µg/ml As is clear from the results in Table 2, the polysaccharide sample (containing the neutral polysaccharide fractions and acidic polysaccharide fractions), the neutral polysaccharide fractions and acidic polysaccharide fractions, which were exopolysaccharides produced by the strain IJH-SONE68, exhibited a high hyaluronidase inhibitory activity. In particular, the polysaccharide sample and the neutral polysaccharide fractions exhibited a hyaluronidase inhibitory activity comparable to that of dipotassium glycyrrhizinate having anti-inflammatory action.

Example 6

Acid Resistance Properties of the Strain IJH-SONE68

In order to investigate the acid resistance properties of the strain IJH-SONE68, acid resistance tests were performed on an artificial gastric juice and an artificial bile.

1. Test of Acid Resistance Against Artificial Gastric Juice
(1) Test Method

An artificial gastric juice was prepared using the first solution (pH 1.2) and second solution (pH 6.8) of a disintegration test in the Japanese Pharmacopoeia (both manufactured by Wako Pure Chemical Industries, Ltd.). Thus, an artificial gastric juice of pH 3.0 containing 0.04 w/v % pepsin (1:10000, manufactured by Wako Pure Chemical Industries, Ltd.) was prepared. A seed culture solution of the strain IJH-SONE68, which had been statically cultured in MRS liquid medium until a stationary state, was inoculated to the artificial gastric juice at a certain amount, and the viable cells were counted after 1, 3 and 5 hours. Taking the number of the viable cells at the inoculation time as 100%, the survival rate was obtained. When measuring the number of the viable cells, a part of the solution after each lapse of time was appropriately serially diluted, and pour-cultured (37° C., anaerobic condition, several days) using BCP-plated plate count agar (Nissui Pharmaceutical), and the number of the viable bacteria present in the diluted solution was calculated by counting the number of colonies formed on the agar. At the same time, the tests were also performed on *Lactobacillus bulgaricus* B-5b (http://www.ge-ne.affrc.go.jp/databases-micro_search_detail.php?maff=401001).

(2) Test Results

Table 3 shows the obtained results of the acid resistance tests.

TABLE 3

Resistance against artificial gastric juice

| | Turbidity (%) of bacterial cell bodies after static culture | |
|---|---|---|
| Culture time | IJH-SONE68 | *Lactobacillus bulgaricus* B-5b |
| Without artificial gastric juice | 100 | 100 |
| 1 hour | 74.42 | 0 |
| 3 hours | 68.30 | 0 |
| 5 hours | 37.69 | 0 |

As is clear from the results in Table 3, the strain IJH-SONE68 had a high acid resistance property against the artificial gastric juice, as compared with *Lactobacillus bulgaricus* B-5b.

2. Test of Acid Resistance Against Artificial Bile
(1) Test Method

MRS liquid medium containing 0.1, 0.2 or 0.3 w/v % bile powders (manufactured by Wako Pure Chemical Industries, Ltd.) was prepared, and 0.1 v/v % seed culture solution of the strain IJH-SONE68, which had been statically cultured in MRS liquid medium until a stationary state, was inoculated on the prepared MRS liquid medium, and statically cultured at 37° C. for 24 hours. After the completion of the culture, the turbidity (O.D. 600 nm) of the bacterial cell bodies in the MRS medium not containing bile powders was taken as 100%, and the ratio of the turbidity of the bacterial cell bodies in the MRS medium containing bile powders at each concentration was calculated. At the same time, the tests were also performed on *Lactobacillus acidophilus* L-54 (provided by the Japan Dairy Technology Association) and *Lactobacillus bulgaricus* B-5b.

(2) Test Results

Table 4 shows the obtained results of the acid resistance tests.

TABLE 4

Resistance against artificial bile

| | Turbidity (%) of bacterial cell bodies after static culture for 24 hours | | |
|---|---|---|---|
| Concentration of bile powders | IJH-SONE68 | *Lactobacillus acidophilus* L-54 | *Lactobacillus bulgaricus* B-5b |
| Without bile powders | 100 | 100 | 100 |
| 0.1 w/v % | 56.35 | 3.98 | 0.32 |
| 0.2 w/v % | 6.11 | 0 | 0 |
| 0.3 w/v % | 5.21 | 0 | 0 |

As is clear from the results in Table 4, the strain IJH-SONE68 had a high acid resistance against the artificial bile, as compared with *Lactobacillus acidophilus* L-54 and *Lactobacillus bulgaricus* B-5b.

Example 7

Effect of the Strain IJH-SONE68 on Alcoholic Damage

The influence of the strain IJH-SONE68 on alcoholic hepatitis-induced mouse models were investigated to study the effect of the strain IJH-SONE68 on alcoholic damage.

1. Test Method

Alcoholic hepatitis-induced mouse models were prepared by allowing C57BL/6J male mice having alcohol taste (Japan CLEA, 8 weeks of age) to ingest ethanol-containing feeds for 6 weeks. During that period, it was observed how the presence or absence of the ingestion of lactic acid bacteria had an influence on the mouse models. Specifically, during the breeding period, mice were divided into the following three groups ((1)-(3)) according to differences in the diets, blood was collected 6 weeks after the start of the breeding.

1): Positive control group (ethanol-containing feed L10016 only):
2): Negative control group (ethanol-free feed L10015 only)
3): IJH-SONE68-administered group (ethanol-containing feed L10016+ viable cell bodies of lactic acid bacteria)
Ethanol-containing feed L10016: prepared by mixing Pre-Mix L10016A (Research Diet Co.) with water and ethanol immediately before use.
Ethanol-free feed L10015: prepared by mixing Pre-Mix L10016A (Research Diet) with water and maltodextrin immediately before use.

Mice were purchased at 7 weeks of age, and 5 mice were divided per group. The mice were bred with normal diets (MF manufactured by Oriental Yeast Co., Ltd.) for one week to be habituated, and then subjected to experiments. The breeding was carried out at the Kasumi Animal Experimental Facility in Kasumi Campus, the Hiroshima University. During the breeding period, the humidity was maintained at 40 to 60%, and the air temperature was maintained at 20 to 26° C. The breeding was carried out in circumstances where ON/OFF of the lighting was able to be switched every 12 hours. Individual mice were identified by painting their tails with an animal marker (manufactured by Muromachi Instruments Co., Ltd.) (distinguished by red, blue, green, yellow and no coloring).

The diets used in the tests were those obtained by culturing each lactic acid bacterium strain in MRS medium and washing and mixing it with ethanol feed. During the experiments, the diet in a feeding container was changed every day, and the mice were allowed to freely access to the diet. Any other diets including water were not given the mice. In addition, the remaining amount of the diets was also measured. After 6 weeks passed from the start of the breeding, the mice were euthanized by isoflurane inhalation and intraperitoneal administration of pentobarbital, and blood was collected. Serum collected from the blood was frozen-stored at −80° C. Blood biochemical examinations were performed to measure the values of AST (aspartate aminotransferase), ALT (alanine aminotransferase), ALP (alkaline phosphatase), LDH (lactate dehydrogenase), LAP (Leucine aminopeptidase) and LIP (lipase) in the serum, which are indications for investigating alcoholic damage. Statistical analysis of each measured value was made by SPSS 17.0 (SPSS Japan).

2. Test Results

The graphs of FIGS. 7 to 12 illustrate the measured values (IU/L) of AST, ALT, ALP, LDH, LAP and LIP for the positive control group (PC), the negative control group (NC) and the strain IJH-SONE68-administered group (SONE68). As can be seen from the graphs of FIGS. 7 to 12, the strain IJH-SONE68 decreased the values of AST, ALT, ALP, LDH, LAP and LIP as compared with the positive control group (PC), and showed excellent preventive improvement effects on alcoholic damage.

Example 8

Application of the Strain IJH-SONE68 to Puree

An example in which the strain IJH-SONE68 was applied to a puree containing fig fruit, sake lees and the like is described below.

Fig fruits were cut to an appropriate size, and 1.0 (w/w) % cellulase "Onozuka" 3S, 0.5 (w/w) % pectinase 3S, 0.5 (w/w) % sodium ascorbate, sake lees (brewing byproduct) powders and 100 (w/w) % pure water were added to the cut fruits. The whole mixture was treated using an extract device (manufactured by Toyo High Pressure Co., Ltd.) under the conditions of 50° C. and 100 MPa for 24 hours. Specifically, the necessary amount of fig fruits, that had been divided with a kitchen knife so as to be ¼ size almost uniformly, was placed into a processing pouch (hybrid bag, manufactured by Cosmo Bio Co., Ltd.). An aqueous solution containing all of the aforementioned reagents dissolved therein was added to the hybrid bag, air bubbles were removed from the resultant mixture as much as possible, and the hybrid bag was sealed with a sealer (Policyler, manufactured by ASONE Corporation). After the sealing, the whole bag was placed into an extract device (2 L type, manufactured by Toyo High Pressure Co., Ltd.) and treated under the aforementioned conditions. Before cultivation, the pouch was opened aseptically in a clean bench (manufactured by SANYO Corporation) (with scissors sterilization-treated with alcohol), and the contents in the pouch were aseptically transferred into a container (Aiboi, ASONE Corporation) that had been in advance sterilized by a high-pressure sterilization machine (manufactured by Tommy Seiko Co., Ltd.).

A bacterial cell suspension of *Lactobacillus paracasei* strain IJH-SONE68, that had been in advance seed-cultured in MRS medium at 37° C. for 2 to 3 days, was added to the prepared puree such that the added amount became one corresponding to 1 (v/v) %, and statically cultured at 37° C. for 48 hours. Specifically, first, MRS medium (manufactured by Merck & Co., Inc.) dispensed in 10 mL portion into a threaded test tube was autoclaved at 118° C. for 15 minutes, and the bacterial stock of the strain IJH-SONE68 frozen-stored at −80° C. was inoculated on the MRS medium in a clean bench. After stoppered, it was cultured in an incubator at 37° C. for 2 to 3 days while standing the test tube on a test tube stand. After the culture, the contents were inverted-mixed until the turbidity of the culture solution became homogeneous, and the contents were transferred into a centrifuge tube with 15 mL volume (manufactured by Nunc) in a clean bench. After the bacterial cell bodies were precipitated by centrifugation (manufactured by Eppendorf), the culture supernatant was discarded in a clean bench, and puree was then added in an amount of 10 mL. After stoppered, the bacterial cells precipitated by a vortex machine (manufactured by Scientific Industries) were resuspended. Thereafter, a necessary amount of the bacteria-suspended puree was added to the puree in a clean bench and, after stoppered, cultured in an incubator (manufactured by Yamato Scientific Co., Ltd.) at 37° C. for 2-3 days, while standing the bottle.

The puree obtained by the foregoing processes had a good texture and flavor as compared with puree obtained without addition of the bacterial cell suspension.

Example 9

Culture Using Egg White Medium

The strain IJH-SONE68 was cultured using an egg white medium and its proliferation was investigated.

1. Preparation and Cultivation of Egg White Medium (1). Method

Chicken eggs, which were lightly disinfected with ethanol while having their shells, were broken in a clean bench, and divided into egg yolk and egg white, and only the egg white part was obtained. The egg white was placed into a 50 mL conical tube, agitated by vortex to have a homogeneous viscosity, and then aliquoted into other tubes at a uniform volume for culture.

A culture liquid of the lactic acid bacteria of the seed-cultured strain IJH-SONE68 was aseptically inoculated on each of the above tubes at a final concentration of 1 v/v %, and statically cultured. Likewise, the culture was performed using other lactic acid bacterium, *Pediococcus pentosaceus* (strain LP28).

(2). Results

Figure 13:
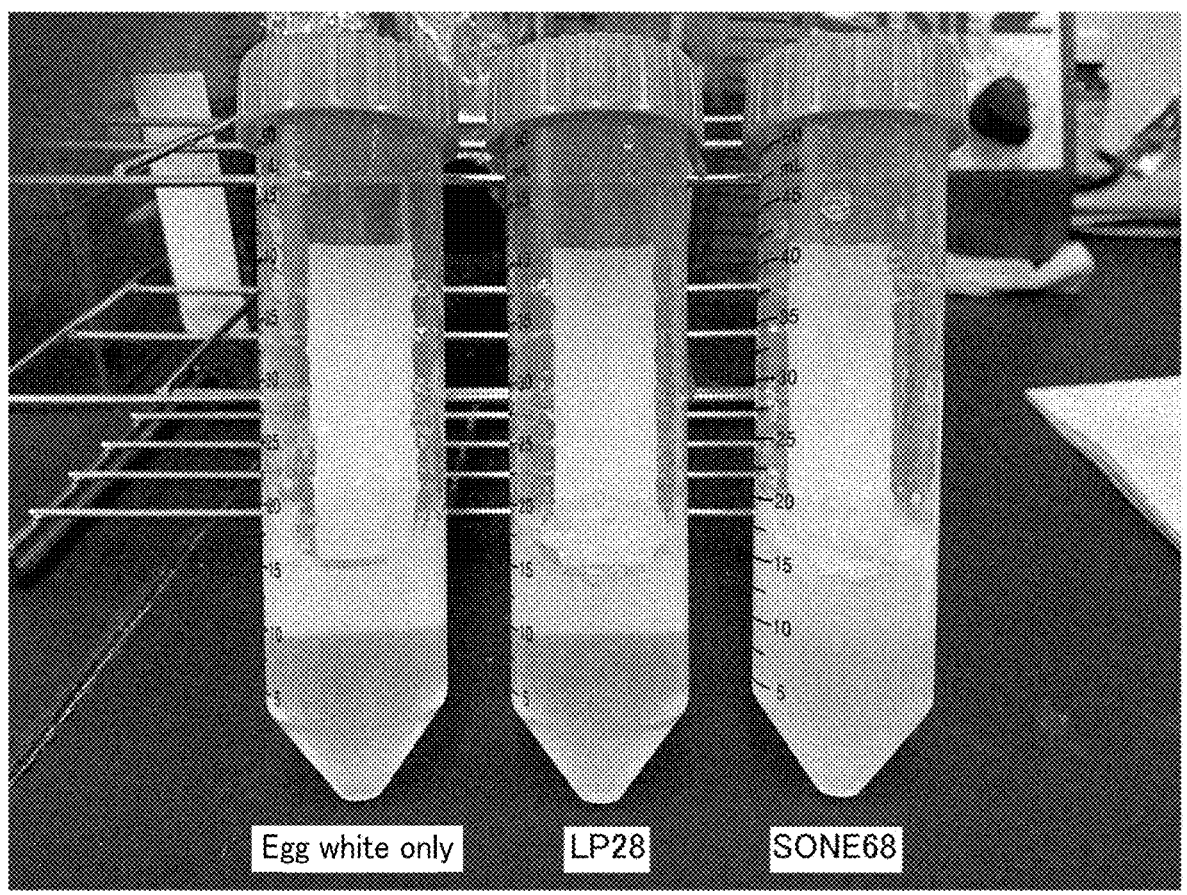
FIG. 13 illustrates results of culturing *Lactobacillus paracasei* strain IJH-SONE68 in a medium using egg white.

FIG. 13 illustrates the culture results. As can be seen from FIG. 13, the lactic acid bacteria of the strain IJH-SONE68 proliferated very much in the medium using egg white.

2. Preparation and Cultivation of Medium in which Glucose and Bittern were Added to Egg White (1). Method When making the cultivation according to the method 1 above, glucose was added to egg white so that the final concentration became 1 w/v %, and bittern (its composition: Nat: 92 mg; $Ca^{2+}$: 3, 500 mg; $Mg^{2+}$: 6,400 mg; and $K^+$: 2,300 mg) was further added to egg white so that the final concentration became 1 v/v %, and then cultured. Specifically, before culturing the lactic acid bacteria, 10 w/v % glucose aqueous solution that had been subjected to a filter sterilization treatment was added to the lactic acid bacteria at $\frac{1}{10}$ volume of the egg white, and bittern sterilized with a filter was also added to egg white at $\frac{1}{100}$ volume of the egg, followed by being cultured.

(2). Results

Figure 14:
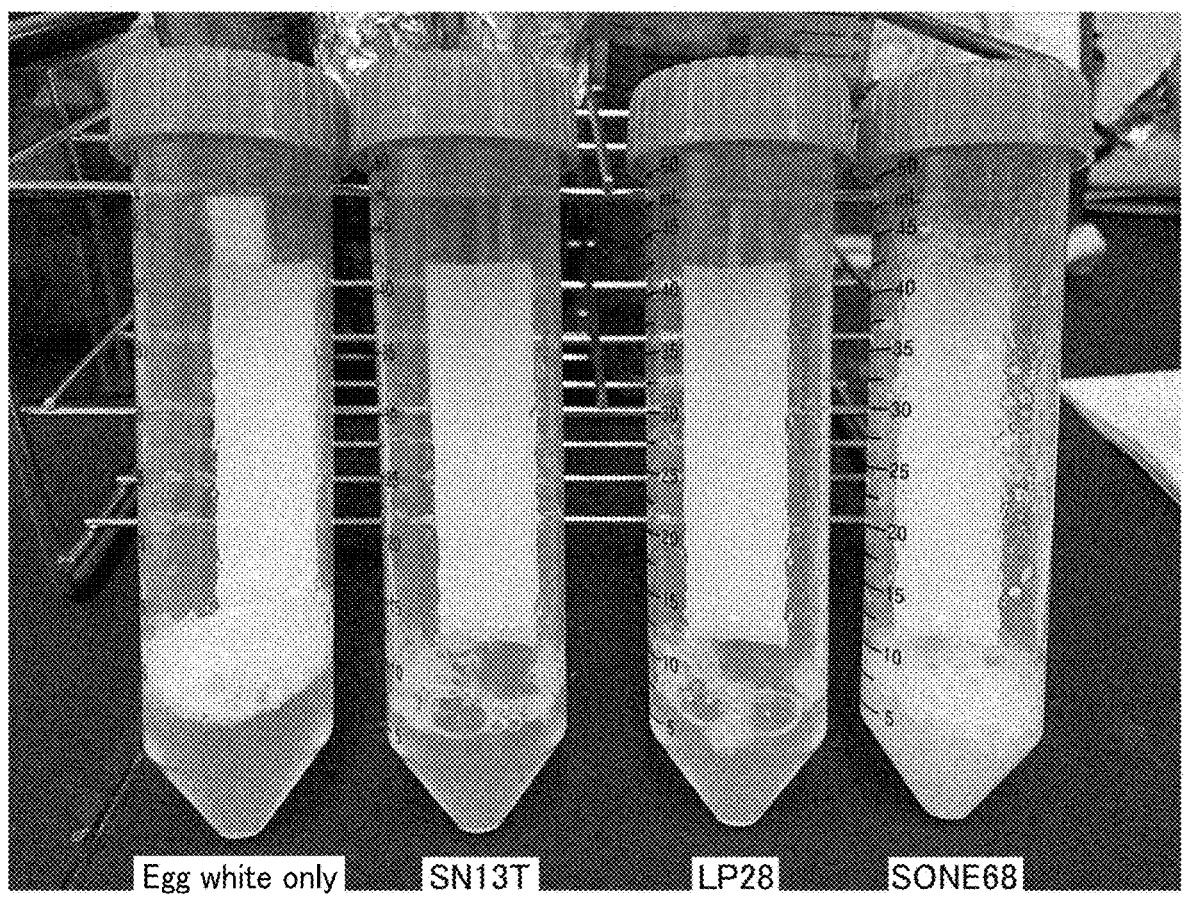
FIG. 14 illustrates results of culturing *Lactobacillus paracasei* strain IJH-SONE68 in a medium in which egg whites were supplemented with glucose and bittern.

FIG. 14 illustrates the culture results. As can be seen from FIG. 14, the lactic acid bacteria of the strain IJH-SONE68 remarkably proliferated in the medium in which glucose and bittern were added to egg white.

From these results, it was revealed that since the lactic acid bacteria of the strain IJH-SONE68 exerted a strong proliferation ability even in the medium using egg white, they had a strong defense mechanism against lysozyme degrading bacterial cell wall and transferrin interfering the iron utilization of bacteria by their chelating action, which are enzymes present in egg white.

As is clear from the foregoing detailed descriptions, the present invention provides the following inventions:

[1] A lactic acid bacterium which produces, as an exopolysaccharide, a neutral polysaccharide having a structure in which N-acetylglucosamines are linked with each other via α-1,6 bond;

[2] The lactic acid bacterium according to the above [1], which belongs to the genus *Lactobacillus*;

[3] The lactic acid bacterium according to the above [1] or [2], which belongs to *Lactobacillus paracasei*;

[4] The lactic acid bacterium according to any one of the above [1] to [3], which is derived from a fig;

[5] The lactic acid bacterium according to any one of the above [1] to [4], which is *Lactobacillus paracasei* strain IJH-SONE68 (Accession No. NITE BP-02242) or a lactic acid bacterium equivalent thereto;

[6] The lactic acid bacterium according to any one of the above [1] to [5], wherein the neutral polysaccharide has a hyaluronidase inhibitory activity;

[7] A composition comprising the lactic acid bacterium according to any one of the above [1] to [6];

[8] The composition according to the above [7], which is a food and drink composition;

[9] The composition according to the above [8], wherein the food and drink are a beverage, a functional food, a fermented food or a supplement;

[10] The composition according to the above [7], which is a pharmaceutical composition;

[11] The composition according to the above [7], which is a feed composition;

[12] The composition according to the above [7], which is a cosmetic composition;

[13] The composition according to any one of the above [7] to [12], which is for hyaluronidase inhibition;

[14] The composition according to any one of the above [7] to [12], which is for an antiallergy;

[15] The composition according to any one of the above [7] to [12], which is for an anti-alcoholic damage;

[16] Use of the lactic acid bacterium according to any one of the above [1] to [6] as an active ingredient of a composition;

[17] The use according to the above [16], wherein the composition is a food and drink composition;

[18] The use according to the above [17], wherein the food and drink are a beverage, a functional food, a fermented food or a supplement;

[19] The use according to the above [16], wherein the composition is a pharmaceutical composition;

[20] The use according to the above [16], wherein the composition is a feed composition;

[21] The use according to the above [17], wherein the composition is a cosmetic composition;

[22] The use according to any one of the above [16] to [21], wherein the composition is for a hyaluronidase inhibition;

[23] The use according to any one of the above [16] to [21], wherein the composition is for an antiallergy;

[24] The use according to any one of the above [16] to [21], wherein the composition is for an anti-alcoholic damage;

[25] A method for preparing a composition, comprising mixing the lactic acid bacterium according to any one of the above [1] to [6] with another component;

[26] The preparation method according to the above [25], wherein the composition is a food and drink composition;

[27] The preparation method according to the above [26], wherein the food and drink are a beverage, a functional food, a fermented food or a supplement;

[28] The preparation method according to the above [25], wherein the composition is a pharmaceutical composition;

[29] The preparation method according to the above [25], wherein the composition is a feed composition;

[30] The preparation method according to the above [25], wherein the composition is a cosmetic composition;

[31] The preparation method according to any one of the above [25] to [30], wherein the composition is for a hyaluronidase inhibition;

[32] The preparation method according to any one of the above [25] to [30], wherein the composition is for an antiallergy;

[33] The preparation method according to any one of the above [25] to [30], wherein the composition is for an anti-alcoholic damage;

[34] A method for applying the lactic acid bacterium according to any one of the above [1] to [6] to a subject in need thereof, the method comprising applying a composition comprising the lactic acid bacterium according to any one of the above [1] to [6] to the subject;

[35] The application method according to the above [34], wherein the composition is a food and drink composition;

[36] The application method according to the above [34], wherein the food and drink are a beverage, a functional food, a fermented food or a supplement;

[37] The application method according to the above [34], wherein the composition is a pharmaceutical composition;

[38] The application method according to the above [34], wherein the composition is a feed composition;

[39] The application method according to the above [34], wherein the composition is a cosmetic composition;

[40] The application method according to any one of the above [34] to [39], wherein the composition exerts a hyaluronidase inhibition action to the subject;

[41] The application method according to any one of the above [34] to [39], wherein the composition exerts an antiallergy action on the subject; and

[42] The application method according to any one of the above [34] to [39], wherein the composition exerts an anti-alcoholic damage on the subject.

INDUSTRIAL APPLICABILITY

As described in detail herein above, the lactic acid bacterium of the present invention produces an exopolysaccharide exerting a hyaluronidase inhibitory activity and exhibiting an antiallergy effect and, in addition, exhibits an anti-alcoholic damage effect. Furthermore, the lactic acid bacterium of the present invention has a high resistance against gastric acid and bile acid, and exerts a strong proliferation ability even in a medium using egg white. Therefore, the lactic acid bacterium of the present invention can be used as an active ingredient of a food and drink, a medicine, a feed, a cosmetic and the like.

The invention claimed is:

1. A method for preparing a composition, comprising:
   providing a *Lactobacillus paracasei* strain IJH-SONE68 (Accession No. NITE BP-02242) bacterium; and
   mixing the *Lactobacillus paracasei* strain IJH-SONE68 (Accession No. NITE BP-02242) bacterium with a physiologically acceptable liquid or solid pharmaceutical carrier, a food and drink, a feed, or a cosmetic to make the composition,
   wherein the *Lactobacillus paracasei* strain IJH-SONE68 (Accession No. NITE BP-02242) bacterium is present at a concentration of $1\times10^6$ cfu/g to $1\times10^{12}$ cfu/g, $1\times10^6$ cfu/ml to $1\times10^{12}$ cfu/ml, $1\times10^6$ cells/g to $1\times10^{12}$ cells/g, or at least 0.001% by weight.

2. The method of claim 1, wherein the composition is a food and drink composition, a pharmaceutical composition, a feed composition, or a cosmetic composition.

3. The method of claim 2, wherein the food and drink composition is a functional food, a fermented food, or a supplement.

4. A method for improving or preventing allergy, comprising administering a composition to a subject in need thereof, said composition comprising a *Lactobacillus paracasei* strain IJH-SONE68 (Accession No. NITE BP-02242) bacterium and a physiologically acceptable liquid or solid pharmaceutical carrier, a food and drink, a feed, or a cosmetic,
   wherein the *Lactobacillus paracasei* strain IJH-SONE68 (Accession No. NITE BP-02242) bacterium is present at a concentration of $1\times10^6$ cfu/g to $1\times10^{12}$ cfu/g, $1\times10^6$ cfu/ml to $1\times10^{12}$ cfu/ml, $1\times10^6$ cells/g to $1\times10^{12}$ cells/g, or at least 0.001% by weight.

5. A method for improving or preventing alcoholic damage, comprising administering a composition to a subject in need thereof, said composition comprising a *Lactobacillus paracasei* strain IJH-SONE68 (Accession No. NITE BP-02242) bacterium and a physiologically acceptable liquid or solid pharmaceutical carrier, a food and drink, a feed, or a cosmetic,
   wherein the *Lactobacillus paracasei* strain IJH-SONE68 (Accession No. NITE BP-02242) bacterium is present at a concentration of $1\times10^6$ cfu/g to $1\times10^{12}$ cfu/g, $1\times10^6$ cfu/ml to $1\times10^{12}$ cfu/ml, $1\times10^6$ cells/g to $1\times10^{12}$ cells/g, or at least 0.001% by weight.

6. The method according to claim 4, wherein said composition is a food and drink composition, a pharmaceutical composition, a feed composition or a cosmetic composition.

7. The method according to claim 6, wherein the food and drink are a beverage, a functional food, a fermented food or a supplement.

8. The method according to claim 5, wherein said composition is a food and drink composition, a pharmaceutical composition, a feed composition or a cosmetic composition.

9. The method according to claim 8, wherein the food and drink are a beverage, a functional food, a fermented food or a supplement.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agagtttgat cctggctcag                                              20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaggaggtg atccagcc                                                18

<210> SEQ ID NO 3
<211> LENGTH: 1549
<212> TYPE: DNA
<213> ORGANISM: Lactobacillus sp.

<400> SEQUENCE: 3
atttatatga gagtttgatc ctggctcagg atgaacgctg gcggcgtgcc taatacatgc    60
aagtcgaacg agttctcgtt gatgatcggt gcttgcaccg agattcaaca tggaacgagt   120
ggcggacggg tgagtaacac gtgggtaacc tgcccttaag tggggataa catttggaaa    180 cagatgctaa taccgcatag atccaagaac cgcatggttc ttggctgaaa gatggcgtaa   240
gctatcgctt ttggatggac ccgcggcgta ttagctagtt ggtgaggtaa tggctcacca   300
aggcgatgat acgtagccga actgagaggt tgatcggcca cattgggact gagacacggc   360
ccaaactcct acgggaggca gcagtaggga atcttccaca atggacgcaa gtctgatgga   420
gcaacgccgc gtgagtgaag aaggctttcg ggtcgtaaaa ctctgttgtt ggagaagaat   480
ggtcggcaga gtaactgttg tcggcgtgac ggtatccaac cagaaagcca cggctaacta   540
```

```
cgtgccagca gccgcggtaa tacgtaggtg gcaagcgtta tccggattta ttgggcgtaa    600
agcgagcgca ggcggttttt taagtctgat gtgaaagccc tcggcttaac cgaggaagcg    660
catcggaaac tgggaaactt gagtgcagaa gaggacagtg gaactccatg tgtagcggtg    720
aaatgcgtag atatatggaa gaacaccagt ggcgaaggcg gctgtctggt ctgtaactga    780
cgctgaggct cgaaagcatg ggtagcgaac aggattagat accctggtag tccatgccgt    840
aaacgatgaa tgctaggtgt tggagggttt ccgcccttca gtgccgcagc taacgcatta    900
agcattccgc ctggggagta cgaccgcaag gttgaaactc aaaggaattg acggggccc     960
gcacaagcgg tggagcatgt ggtttaattc gaagcaacgc gaagaacctt accaggtctt   1020
gacatctttt gatcacctga gagatcaggt ttccccttcg ggggcaaaat gacaggtggt   1080
gcatggttgt cgtcagctcg tgtcgtgaga tgttgggtta agtcccgcaa cgagcgcaac   1140
ccttatgact agttgccagc atttagttgg gcactctagt aagactgccg gtgacaaacc   1200
ggaggaaggt ggggatgacg tcaaatcatc atgcccctta tgacctgggc tacacacgtg   1260
ctacaatgga tggtacaacg agttgcgaga ccgcgaggtc aagctaatct cttaaagcca   1320
ttctcagttc ggactgtagg ctgcaactcg cctacacgaa gtcggaatcg ctagtaatcg   1380
cggatcagca cgccgcggtg aatacgttcc cgggccttgt acacaccgcc cgtcacacca   1440
tgagagtttg taacacccga agccggtggc gtaacccttt tagggagcga gccgtctaag   1500
gtgggacaaa tgattagggt gaagtcgtaa caaggtagcc gtaggagaa              1549
```